United States Patent
Zhong et al.

(10) Patent No.: US 10,336,720 B2
(45) Date of Patent: Jul. 2, 2019

(54) CYCLIC CARBONATE MONOMER CONTAINING DOUBLE IODINE, BIODEGRADABLE POLYMER PREPARED THEREBY AND USE

(71) Applicant: SOOCHOW UNIVERSITY, Suzhou (CN)

(72) Inventors: Zhiyuan Zhong, Suzhou (CN); Yan Zou, Suzhou (CN); Yaohua Wei, Suzhou (CN); Fenghua Meng, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 89 days.

(21) Appl. No.: 15/550,787

(22) PCT Filed: Feb. 12, 2016

(86) PCT No.: PCT/CN2016/073743
§ 371 (c)(1),
(2) Date: Aug. 13, 2017

(87) PCT Pub. No.: WO2016/127940
PCT Pub. Date: Aug. 18, 2016

(65) Prior Publication Data
US 2018/0044315 A1    Feb. 15, 2018

(30) Foreign Application Priority Data

Feb. 13, 2015 (CN) .......................... 2015 1 0077770
Feb. 13, 2015 (CN) .......................... 2015 1 0077784

(51) Int. Cl.
| | | |
|---|---|---|
| C07D 319/06 | (2006.01) | |
| A61L 27/18 | (2006.01) | |
| A61K 31/704 | (2006.01) | |
| A61K 47/34 | (2017.01) | |
| C08G 64/02 | (2006.01) | |
| A61L 27/58 | (2006.01) | |
| A61K 49/04 | (2006.01) | |
| B82Y 30/00 | (2011.01) | |
| B82Y 40/00 | (2011.01) | |
| C08G 64/30 | (2006.01) | |
| C08G 63/64 | (2006.01) | |

(52) U.S. Cl.
CPC .......... *C07D 319/06* (2013.01); *A61K 31/704* (2013.01); *A61K 47/34* (2013.01); *A61K 49/0442* (2013.01); *A61L 27/18* (2013.01); *A61L 27/58* (2013.01); *B82Y 30/00* (2013.01); *B82Y 40/00* (2013.01); *C08G 63/64* (2013.01); *C08G 64/025* (2013.01); *C08G 64/0233* (2013.01); *C08G 64/30* (2013.01); *C08G 2230/00* (2013.01)

(58) Field of Classification Search
None
See application file for complete search history.

(56) References Cited

U.S. PATENT DOCUMENTS 6,103,255 A * 8/2000 Levene ............... A61L 27/3839
424/426
2014/0058058 A1* 2/2014 Song ...................... A61L 27/18
528/271

FOREIGN PATENT DOCUMENTS

| CN | 102090392 A | 6/2011 |
| CN | 104610538 A | 5/2015 |
| CN | 104672199 A | 6/2015 |

OTHER PUBLICATIONS

Zhu, et al., "Amphiphilic PEG-Grafted Poly(ester-carbonate)s: Synthesis and Diverse Nanostructures in Water", Polymer Chemistry, 49, 4886-4893, Published online Sep. 9, 2011. (Year: 2011).*
Profiles of Drug Substances, Excipients and Related Methodology, p. 207, Jan. 28, 1991. (Year: 1991).*
Pace, et al. "The Finkelstein Reaction: Quantitative Reaction Kinetics of an Sn2 Reaction using Nonaqueous Conductivity", Journal of Chemical Education, 83 (9), p. 1344-1348, Sep. 9, 2006. (Year: 2006).*
Kelly, "Finkelstein Reaction of 3-Chloro-1-Propanol with Sodium Iodide; 3-Iodo-1-Propanol", Chemspider Synthetic Pages, pp. 551, Apr. 6, 2012. (Year: 2012).*
Wang, Ying et al., "Reductively and Hydrolytically Dual Degradable Nanoparticles by "Click" Crosslinking of a Multifunctional Diblock Copolymer", Polym. Chem., vol. 4, No. 5, Dec. 31, 2013 (Dec. 31, 2013), pp. 1657-1663.
Zhang, Qiujin et al., "Synthesis and Characterization of Biodegradable Amphiphilic PEG-Grafted Poly(DTC-co-CL)", Chinese Chemical Letters, No. 21, Dec. 31, 2010 (Dec. 31, 2010), pp. 1255-1258.
Shi, Quan et al., "Synthesis and Characterization of Azido- and Amino-bearing Aliphatic Polyesters", Chemical Journal of Chinese Universities, vol. 29, No. 7, Jul. 31, 2008 (Jul. 31, 2008), pp. 1492-1494.

(Continued)

*Primary Examiner* — Christopher M Rodd
(74) *Attorney, Agent, or Firm* — SZDC Law P.C.

(57) ABSTRACT

The disclosure relates to a cyclic carbonate monomer containing double iodine, a biodegradable polymer prepared thereby and use. The polymer can be obtained by ring-opening polymerization of the cyclic carbonate monomer containing double iodine, without affecting the ring-opening polymerization and without a protection and deprotection process. The polymer which is obtained by ring-opening polymerization of the cyclic carbonate monomer of the present disclosure can be assembled into a nano-vesicle and a micelle as a drug carrier, a biological tissue scaffold or a CT contrast media.

4 Claims, 10 Drawing Sheets

(56) References Cited

OTHER PUBLICATIONS

Gou, Pengfei et al., "Drug-Grafted Seven-Arm Amphiphilic Star Poly(Caprolactone-co-tonerbonate)-B-Poly (Ethylene Glycol)s Based on a Cyclodextrin Core: Synthesis and Self-Assembly Behavior in Water", Polym.Chem., vol. 1, No. 8, Dec. 31, 2010 (Dec. 31, 2010), pp. 1205-1214.
Chopin, S. et al., "[60]Fullerene Diol Issued from Pentaerythritol Derivatives", Tetrahedron Letters, vol. 46, Dec. 31, 2005 (Dec. 31, 2005), pp. 373-376.

* cited by examiner

CYCLIC CARBONATE MONOMER CONTAINING DOUBLE IODINE, BIODEGRADABLE POLYMER PREPARED THEREBY AND USE

This application is a National Stage Application of PCT/CN2016/073743, filed on Feb. 12, 2016, which claims priority to Chinese Patent Application No. 201510077784.2, filed on Feb. 13, 2015, and Chinese Patent Application No. CN201510077770.0, filed on Feb. 13, 2015, all of which are incorporated by reference for all purposes as if fully set forth herein.

TECHNICAL FIELD

The disclosure relates to a biodegradable polymer material and its application, in particular to a biodegradable polymer containing double iodine and use, belonging to the field of medical material.

BACKGROUND TECHNIQUE

Biodegradable polymers have very unique properties, such as their generally good biocompatibility, degradationity in the body, degradation products can be absorbed by the body or excreted through the body's normal physiological pathway, and is widely used in various biomedical fields, such as surgical sutures, bone fixation devices, bio-tissue engineering scaffold materials, and drug-controlled release carrier et. al. Among them, synthetic biodegradable polymers are of particular interest due to their low immunogenicity, their properties such as degradation and mechanical properties, and the like, can be easily controlled. Synthetic biodegradable polymers are mainly aliphatic polyester, polycarbonate, polyamino acid, polyphosphate, polyanhydride, poly orthoester and so on. Among them, polycarbonates such as polytrimethylene cyclic carbonate (PTMC), aliphatic polyester such as polyglycolide (PGA), polylactide (PLA), lactide-glycolide copolymer (PLGA), polycaprolactone (PCL) and so on are the most commonly used biodegradable polymers, has got the permission of the US Food and Drug Administration (FDA).

However, the existing biodegradable polymers such as PTMC, PCL, PLA and PLGA have simple structure, are lack of functional groups used for modification, thus the medical requirements are hardly satisfied. For example, the drug carriers or the surface modified coatings based on these polymers of these conventional carbonate monomers have fatal weakness of poor stability.

In recent years, many different types of functional biodegradable polymers have been reported in the literature. The researchers particularly interested in biodegradable polymers containing functional groups such as hydroxyl (OH), carboxyl (COOH), amino (NH2), mercapto (SH), etc., since polymers with these functional groups can directly bond drug and accept controlled and sustained release of the drug or the biocompatibility and bioactivity of the entire material can be improved by the attachment of some biologically active molecules to the polymer via functional groups. Functional biodegradable polymers are typically obtained by ring-opening polymerization of functional cyclic monomers, either by deprotection or by further modification. Degradation products of polycarbonate are mainly carbon dioxide and neutral glycol, do not produce acid degradation products. The functional cyclic carbonate monomer can be copolymerized with many cyclic ester monomers such as glycolide (GA), Lactide (LA), caprolactone (ε-CL), and other cyclic carbonate monomers to obtain biodegradable polymers with different properties.

TECHNICAL PROBLEM

In the prior art, in the ring-opening polymerization process, there are reactive groups in the cyclic carbonate monomer structure, and therefore, in the preparation of the functional polymer from the cyclic carbonate monomer, the steps of protection and deprotection are required, it results in a cumbersome preparation process.

MEANS FOR SOLVING THE PROBLEM

Technical Solutions

The aim of the disclosure is to provide a cyclic carbonate monomer containing double iodine and its preparation.

In order to achieve the above-mentioned object, the embodiment of the present disclosure includes: a cyclic carbonate monomer containing double iodine, represented by the following formula:

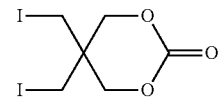

The method for preparing the aforesaid cyclic carbonate monomer containing double iodine includes the following steps: in a low-boiling point solvent, reacting dibromoneopentyl glycol with metal iodide to obtain Compound A; then in nitrogen atmosphere and cyclic ether-based solvent, reacting Compound A with ethyl chloroformate and triethylamine to obtain the cyclic carbonate monomer containing double iodine.

In the aforesaid embodiment, the molar ratio of dibromoneopentyl glycol to metal iodide is 1:(2-4); and the molar ratio of Compound A to ethyl chloroformate and triethylamine is 1:(2-3):(2-3); iodide is potassium iodide or sodium iodide; the low-boiling point solvent generally refers to an organic solvent having a boiling point of not higher than 80° C., such as acetone, methanol, dichloroethane, butanone and the like, and the present disclosure is preferably acetone; the cyclic ether-based solvent preferably tetrahydrofuran.

In a preferred embodiment, after the compound A and the ethyl chloroformate are dissolved in the cyclic ether solvent, the triethylamine is added dropwise, when preparing the cyclic carbonate compound containing double iodine.

In a preferred embodiment, the above-mentioned production method also includes a purification treatment; in detail:

i) Purification of Compound A: sucking filtration is performed after the reaction is completed; the filtrate was further distilled to obtain Compound A as a white solid; ii) Purification of cyclic carbonate compound containing double iodine: filtration is performed after the reaction is completed; the filtrate is concentrated with a rotary evaporator, then recrystallized with ethyl ether to obtain a yellow crystal, which is the cyclic carbonate compound containing double iodine. The aforesaid sucking filtration, evaporation with rotary evaporator, concentration with rotary evaporator and recrystallization all belong to prior art. Those skilled in the art can select the method as desired. In the present disclosure, it is preferable that when purifying the cyclic carbonate compound containing double iodine, recrystallization with ethyl ether is performed 3-5 times.

The disclosure also discloses a kind of biodegradable polymer containing a functional group of double iodine in the side chain, which includes cyclic carbonate monomer containing double iodine, is polymerized of cyclic carbonate monomer containing double iodine by the following steps:

(1) homopolymerize by cyclic carbonate monomer containing double iodine;

(2) cyclic carbonate monomer containing double iodine has copolymerization with other carbonate monomer;

(3) cyclic carbonate monomer containing double iodine has copolymerization with other cyclic ester monomer;

said cyclic carbonate monomer containing double iodine is

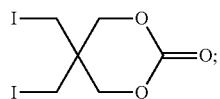

The molecular weight of said biodegradable polymer containing a functional group of double iodine in the side chain is 3-500 kDa.

The amount of iodine in the molecular chain of aforesaid biodegradable polymer containing a functional group of double iodine in the side chain is 5%-65% by mass.

In the above-mentioned technical scheme, the cyclic carbonate monomer containing double iodine is polymerized in the form of polyethylene glycol, ethylene glycol, isopropanol or propynol as the initiator and zinc bis [bis(trimethylsilyl) amide] as the catalyst.

Aforesaid biodegradable polymer containing a functional group of double iodine in the side chain can be prepared from the cyclic carbonate monomer containing double iodine through a ring-opening homopolymerization, or by a ring-opening copolymerization among the cyclic carbonate monomer containing double iodine and other monomer; said other monomer include other carbonate monomer, such as cyclic carbonate containing double-sulfur, 2,4,6-trimethoxy-benzylidene-pentaerythritol carbonate or trimethylene cyclic carbonate (TMC), and include cyclic ester monomer, such as glycolide, caprolactone (ε-CL) or lactide (LA). Since the iodine group does not affect the ring-opening polymerization, the polymerization process does not require the protection and deprotection procedures. When the cyclic carbonate monomer containing double iodine is polymerized, the polymerization temperature is 40° C. and the polymerization time is 24-72 hours.

In the disclosure, the above-mentioned cyclic carbonate monomer containing double iodine can be ring-opening polymerized in the form of polyethylene glycol as the initiator and dichloromethane as the solvent and zinc bis [bis(trimethylsilyl) amide] as the catalyst to form diblock copolymer PEG-b-PIC; The reaction formula is as follows:

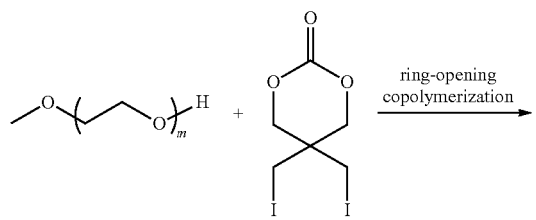

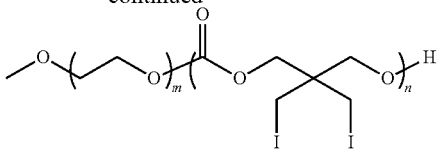

The above-mentioned cyclic carbonate monomer containing double iodine also can be ring-opening copolymerized with other carbonate monomer in the form of dichloromethane as solvent, zinc bis [bis(trimethylsilyl) amide] as the catalyst, polyethylene glycol, ethylene glycol, isopropanol or propynol as the initiator and dichloromethane as the solvent and zinc bis [bis(trimethylsilyl) amide] as the catalyst to form copolymer; the above-mentioned cyclic carbonate monomer containing double iodine also can be ring-opening copolymerized with cyclic ester monomer in the form of dichloromethane as solvent, zinc bis [bis(trimethylsilyl) amide] as the catalyst and polyethylene glycol, ethylene glycol, isopropanol or propynol as the initiator to form copolymer.

The chemical structure of biodegradable polymer containing a functional group of double iodine in the side chain obtained according to the process of the present disclosure is one of the following formulas:

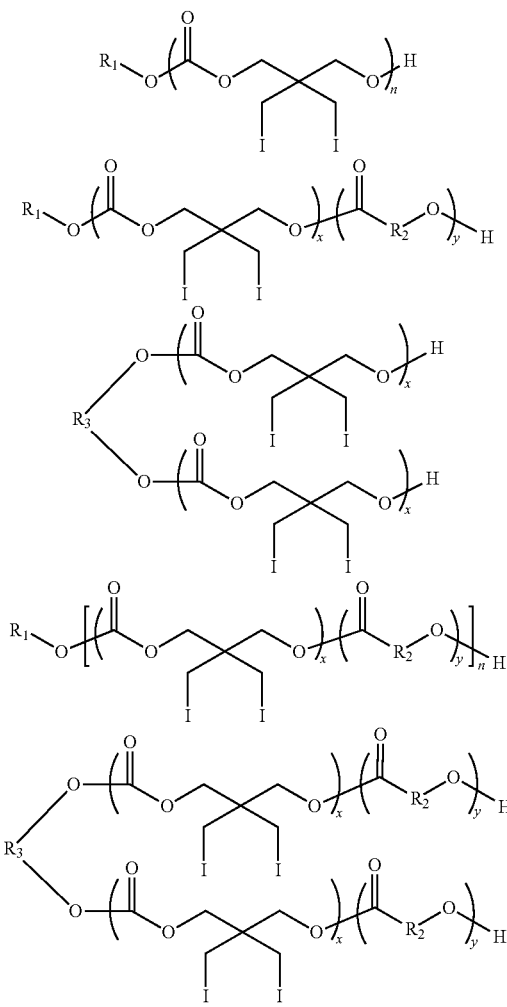

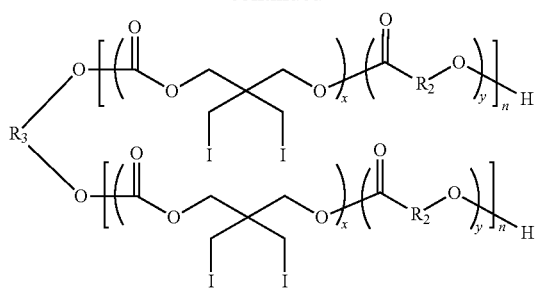

wherein R1 is selected from one of the following groups:

—CH₃, —CH₂—CH₃, —CH(CH₃)₂, —CH₂—CH₂—CH₃,

—CH₂—CH₂—CH₂—CH₃, —CH₂—CH=CH₂,

—CH₂—CH₂—CH=CH₂, —CH₂—C≡CH,

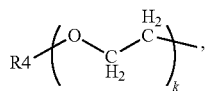

in the formula, k=20-250, R4 is selected from one of the following groups:

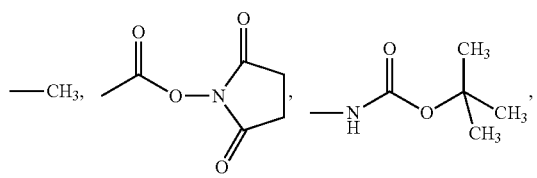

R2 is selected from one of the following groups:

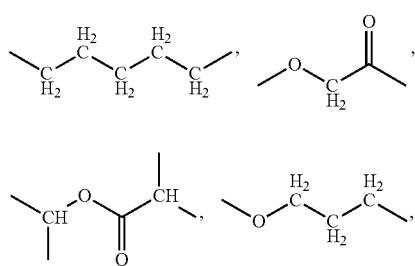

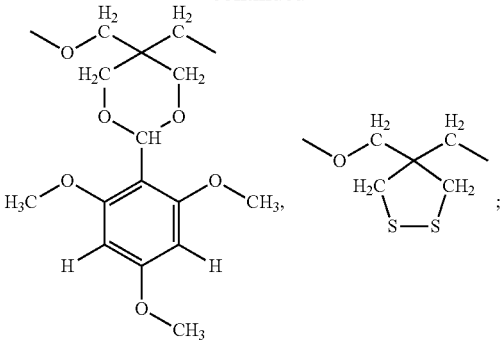

R3 is selected from one of the following groups:

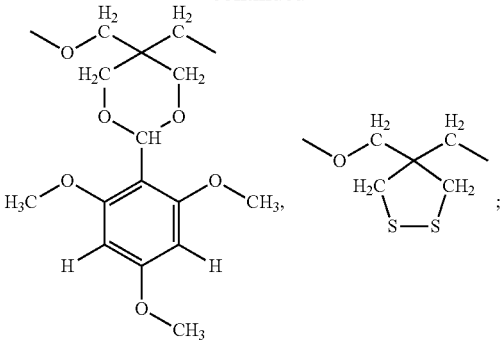

in the formula, a=2, 3 or 4; b=20-250.

The polymer containing iodine obtained by ring-opening polymerization of the cyclic carbonate monomer of the present disclosure and the carbonate monomer containing a functional group of disulfide five-membered ring in the side chain has good biodegradability and may form stable chemical crosslink under catalysis by catalytic amount of reducer like dithiothreitol or glutathione, but it may de-crosslink rapidly in the intracellular reducing environment.; may be used for preparing drug carriers. And the functional biodegradable polymer containing iodine can be used for CT imaging or biological tissue engineering scaffolds because of its special development effect. The above-mentioned biodegradable polymer containing a functional group of double iodine in the side chain can act as a contrast agent and play a role in the diagnosis of the organism.

The present disclosure therefore provides a use of the above-described biodegradable polymer containing a functional group of double iodine in the side chain in the preparation of a drug carrier; said biodegradable polymer containing a functional group of double iodine in the side chain has a molecular weight of 3-50 kDa; the amount of iodine in the molecular chain of aforesaid biodegradable polymer containing a functional group of double iodine in the side chain is 5%-65%.

The present disclosure provides a use of the above-described biodegradable polymer containing a functional group of double iodine in the side chain in the preparation of biological tissue engineering scaffold wherein said biodegradable polymer containing a functional group of double iodine in the side chain has a molecular weight of 5-500 kDa; the amount of iodine in the molecular chain of aforesaid biodegradable polymer containing a functional group of double iodine in the side chain is 35%-65%.

The present disclosure provides a use of the above-described biodegradable polymer containing a functional group of double iodine in the side chain in the preparation of CT contrast agent wherein said biodegradable polymer containing a functional group of double iodine in the side chain has a molecular weight of 100-500 kDa; the amount of iodine in the molecular chain of aforesaid biodegradable polymer containing a functional group of double iodine in the side chain is 35%-65%.

EFFECTS OF THE DISCLOSURE

Beneficial Effects

As a result of the above-mentioned scheme, the disclosure has the following advantages compared with the prior art:

1. The disclosure utilizes the cyclic carbonate monomer containing double iodine functional group for the first time to obtain the biodegradable polymer wherein the molecular weight is controlled, the molecular weight distribution is narrowed by the activity controllable ring-opening homopolymerization or copolymerization with other carbonate monomers and cyclic ester monomers, since the iodine group does not affect the ring-opening polymerization of the cyclic carbonate monomer, the polymerization process does not require the protection and deprotection procedures in the prior art, simplifies the operation steps, overcoming the technical bias in the prior art in the need for protection and deprotection of polymerization of cyclic carbonate.

2. The cyclic carbonate monomer disclosed in the present disclosure is easily to be made, and can conveniently take ring-opening polymerization to obtain biocompatible polymers containing carbonate segments; the polymer can be further used for self-assembly in the controlled-drug release systems, tissue engineering and CT contrast agent, has a good application value in the biological materials.

DETAILED DESCRIPTION OF THE EMBODIMENTS

The present disclosure will further be described in detail below with reference to examples and figs:

Example 1 Synthesis of the Cyclic Carbonate Monomer Containing Double Iodine (IC)

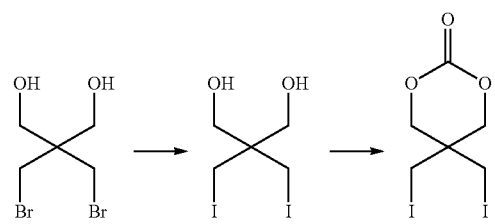

1. Dibromoneopentyl glycol (20 g, 76.4 mmol) was completely dissolved in 300 mL acetone, potassium iodide (25.3 g, 152.4 mmol) was added, condensation reflux reaction was in dark for 24 hours. The reaction was filtered off to remove the resulting potassium bromide and then evaporated to dryness to give the Compound A as a white solid in a yield of 97.5%.

Figure 1:
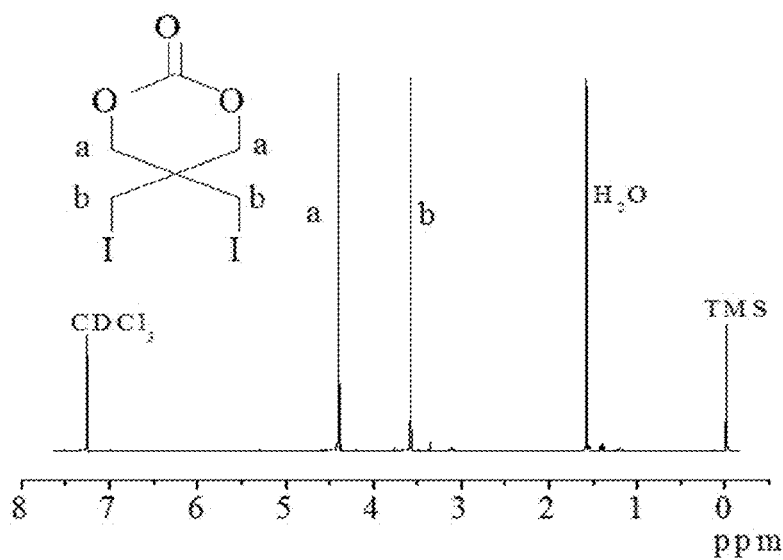
FIG. 1 is an NMR spectrum of the cyclic carbonate monomer containing double iodine in Example 1.

2. Under a nitrogen atmosphere, the Compound A (5 g, 14 mmol) was dissolved in dried THF (150 mL), stirred till completely dissolved, then cooled to 0° C. Ethyl chloroformate (2.81 mL, 29.5 mmol) was added. Then Et$_3$N (4.1 mL, 29.5 mmol) was added dropwise. After finishing the addition, the system was allowed to further react in ice water bath for 4 h. When the reaction was completed, the Et$_3$N.HCl produced was removed through filtration. The filtrate was concentrated with rotary evaporator. Finally, recrystallization was performed several times using ethyl ether, to obtain a white crystal; i.e. the cyclic carbonate monomer containing double iodine (IC), with yield of 32%. FIG. 1 is a $^1$H NMR spectrum of the above product IC (400 MHz, CDCl$_3$): δ 3.62 (s, 4H), 4.43 (s, 4H). Elementary analysis of IC: C: 18.43%, H: 2.05%; O: 12.62% (In theory: C: 18.85%, H: 2.09%, O: 12.56%, I: 66.49%). Mass spectrometry analysis: MS: 381.2 (theoretical molecular weight: 382).

Example 2 Synthesis of the Cyclic Carbonate Monomer Containing Double Iodine (IC)

Dibromoneopentyl glycol (20 g, 76.4 mmol) was completely dissolved in 300 mL acetone, sodium iodide (25.3 g, 152.4 mmol) was added, condensation reflux reaction was in dark for 24 hours. The reaction was filtered off to remove the resulting sodium bromide and then evaporated to dryness to give the Compound A as a white solid in a yield of 95.5%; under a nitrogen atmosphere, the Compound A (5 g, 14 mmol) was dissolved in dried 1,4-epoxy-six-ring (150 mL), stirred till completely dissolved, then cooled to 0° C. Ethyl chloroformate (2.81 mL, 29.5 mmol) was added, then Et$_3$N (4.1 mL, 29.5 mmol) was added dropwise. After finishing the addition, the system was allowed to further react in ice water bath for 4 h. When the reaction was completed, the Et$_3$N.HCl produced was removed through filtration. The filtrate was concentrated with rotary evaporator. Finally, recrystallization was performed several times using ethyl ether, to obtain a white crystal, i.e. the cyclic carbonate monomer containing double iodine (IC), with yield of 23%.

Example 3 Synthesis of Diblock Polymer PEG5k-b-PIC22.7k

Figure 2:
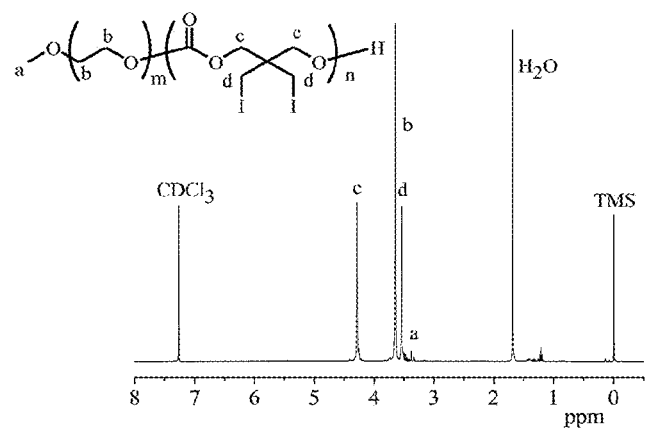
FIG. 2 is an NMR spectrum of the biodegradable polymer containing a group of double iodine in the side chain in Example 3.

In a glove box, 0.6 g (1.57 mmol) IC monomer and 0.1 g (0.02 mmol) polyethylene glycol were dissolved in 3 mL dichloromethane, added to a sealed reactor, and then solution of zinc bis[bis(trimethylsilyl)amide] in dichloromethane (0.1 mol/L) were added. Then the reactor was tightly sealed, put into oil bath at 40° C. The reaction was allowed to proceed for 3 day, and terminated by 2 drops glacial acetic acid, precipitated in ice-cold ethyl ether. Finally, after filtration and vacuum drying, the product PEG5k-b-PIC22.7k was obtained. FIG. 2 is an NMR spectrum of the biodegradable polymer containing a group of double iodine in the side chain. $^1$H NMR (400 MHz, CDCl$_3$): δ 3.30 (—OCH$_3$—), 3.63 (—CCH$_2$—), 3.74 (—CH$_2$CH$_2$—), 4.38 (—CH$_2$CH$_2$—) GPC measured molecular weight: 32.4 kDa, molecular weight distribution: 1.42.

Example 4 Synthesis of Diblock Polymer PEG5k-b-PIC50k

The amount of IC monomer in Example 3 was changed to 1 g (2.61 mmol), and finally the product PEG5k-b-PIC50k was obtained, which was called polymer containing double iodine in the side chain and belonged to biodegradable polymer.

Example 5 Synthesis of Biodegradable Polymer Containing Double Iodine in the Side Chain PEG5k-P(CDC5.6k-Co-IC27.2k)

Figure 3:
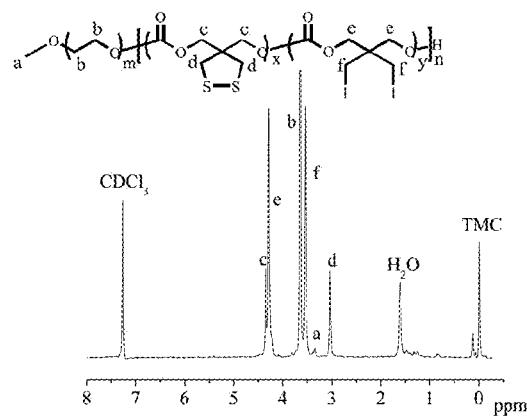
FIG. 3 is an NMR spectrum of the biodegradable polymer containing a group of double iodine in the side chain in Example 5.

Under a nitrogen atmosphere, 0.026 g (0.14 mmol) of carbonate monomer containing double-sulfur five-membered ring (CDC) and 0.13 g (0.34 mmol) carbonate monomer containing double iodine in the side chain (IC) were dissolved in 1 mL dichloromethane, added to a sealed reactor, and then polyethylene glycol having 5000 molecular weight 0.022 g (0.0043 mmol) and 0.1 mol/L catalyst zinc bis[bis(trimethylsilyl)amide] in dichloromethane (0.1 mol/L) were added. Then the reactor was tightly sealed, put into oil bath at 40° C. The reaction was allowed to proceed for 2 days, and terminated by glacial acetic acid, precipitated in ice-cold ethyl ether. Finally, after filtration and vacuum drying, the diblock biodegradable polymer containing a group of double iodine in the side chain PEG5k-P(CDC5.6k-co-IC27.2k) was obtained. FIG. 3 is an NMR spectrum of the polymer. $^1$H NMR (400 MHz, CDCl$_3$): 3.08 (s, —CCH$_2$), 3.64 (s, —CCH$_2$), 3.30 (m, —OCH$_3$), 3.65 (t, —OCH$_2$ CH$_2$O—), 4.25 (m, —CCH$_2$), 4.38 (m, —CCH$_2$); Nuclear magnetic calculations m=113.6, x=29.2, y=71.2, n=100.4, GPC measured molecular weight: 53.2 kDa, molecular weight distribution: 1.42.

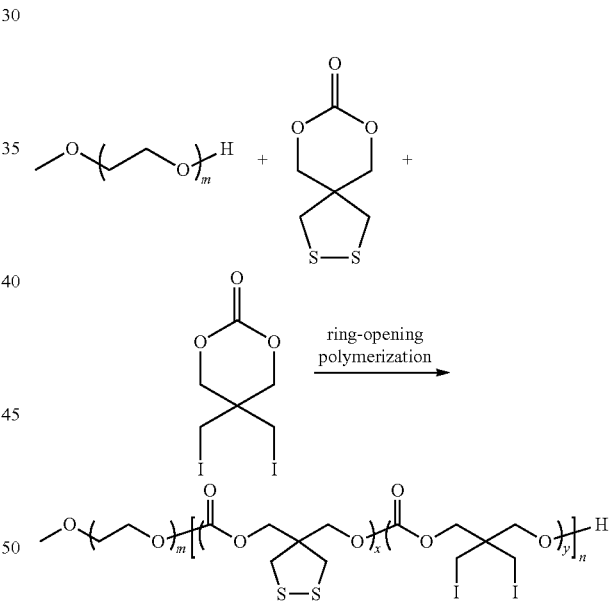

Example 6 Synthesis of Biodegradable Polymer Containing Double Iodine in the Side Chain PEG5k-P(IC4.8k-co-CL14.2k)

Under a nitrogen atmosphere, 0.5 g (1.3 mmol) IC monomer and 1.5 g (13.2 mmol) caprolactone (ε-CL) were dissolved in 10 mL dichloromethane, added to a sealed reactor, and then polyethylene glycol having 5000 molecular weight 0.5 g (0.1 mmol) and 1 mL catalyst zinc bis[bis (trimethylsilyl)amide] in dichloromethane (0.1 mol/L) were added. Then the reactor was tightly sealed and taken out of glove box, put into oil bath at 40° C. The reaction was allowed to proceed for 1 day, and terminated by glacial acetic acid, precipitated in ice-cold ethyl ether. Finally, after filtration and vacuum drying, the PEG5k-P(IC4.8k-co-CL14.2k) was obtained, nuclear magnetic calculations m=113.6, x=122.8, y=13.1, n=135.9, GPC measured molecular weight: 31.3 kDa, molecular weight distribution: 1.42.

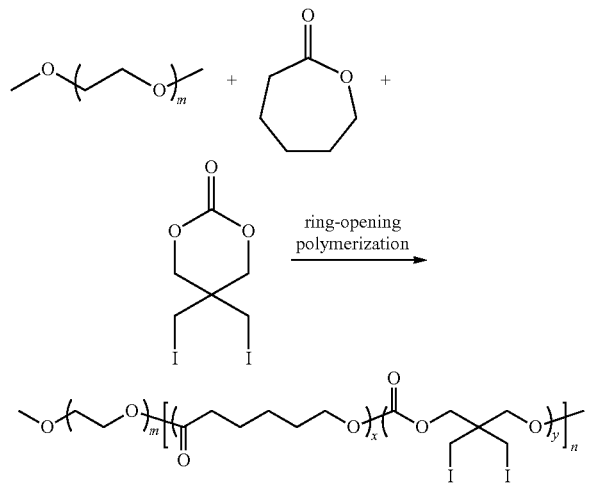

Example 7 Synthesis of Carbonate Homopolymer Containing Double Iodine in the Side Chain Alk-PIC3.8k Under a nitrogen atmosphere, 0.5 g (1.3 mmol) IC monomer was dissolved in 1 mL dichloromethane, added to a sealed reactor, and then purified propargyl alcohol 1 mmol/L and 1 mL catalyst zinc bis[bis(trimethylsilyl)amide] in dichloromethane (0.1 mol/L) were added. Then the reactor was tightly sealed and put into oil bath at 40° C. The reaction was allowed to proceed for 1 day, and terminated by glacial acetic acid, precipitated in ice-cold ethyl ether. Finally, after filtration and vacuum drying, the carbonate homopolymer containing double iodine in the side chain Alk-PIC3.8k was obtained, nuclear magnetic calculations x=12.6, GPC measured molecular weight: 0.62 kDa, molecular weight distribution: 1.28.

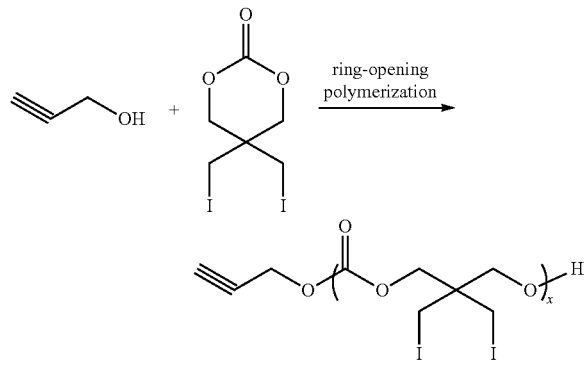

Example 8 Synthesis of Biodegradable Polymer Containing Double Iodine in the Side Chain iPr-P(IC0.7k-co-CL90k)

Under a nitrogen atmosphere, 0.1 g (0.26 mmol) IC monomer and 10 g (87.7 mmol) caprolactone (CL) were dissolved in 10 mL dichloromethane, added to a sealed reactor, and then isopropanol 6 mg (0.1 mmol) and 1 mL catalyst zinc bis[bis(trimethylsilyl)amide] in dichloromethane (0.1 mol/L) were added. Then the reactor was tightly sealed and taken out of glove box, put into oil bath at 40° C. The reaction was allowed to proceed for 2 days, and terminated by glacial acetic acid, precipitated in ice-cold ethyl ether. Finally, after filtration and vacuum drying, the iPr-P(IC0.7k-co-CL90k) was obtained, nuclear magnetic calculations x=1.8, y=78.9, n=80.7, GPC measured molecular weight: 111.3 kDa, molecular weight distribution: 1.53.

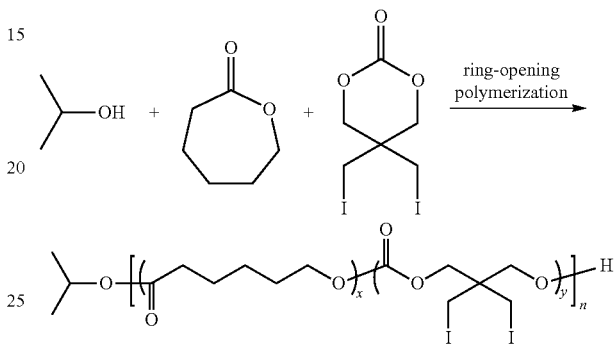

Example 9 Synthesis of Polymer Containing Double Iodine in the Side Chain P(IC-co-CL) (6.21k)-PEG(0.5k)-P(IC-co-CL)(6.21k)

Under a nitrogen atmosphere, 1.5 g (13.2 mmol) caprolactone (ε-CL) and 0.0625 g (0.164 mmol) IC monomer were dissolved in 8 mL dichloromethane, added to a sealed reactor, and then 0.05 g of PEG500 (0.01 mmol) and 1 mL catalyst zinc bis[bis(trimethylsilyl)amide] in dichloromethane (0.1 mol/L) were added. Then the reaction was allowed to proceed in oil bath at 40° C. for 1 day, and terminated by glacial acetic acid, precipitated in ice-cold ethyl ether. Finally, after filtration and vacuum drying, the polymer P(IC-co-CL)(6.21k)-PEG(0.5k)-P(IC-co-CL)(6.21k) was obtained, $^1$H NMR (400 MHz, CDCl$_3$): 1.40 (m, —COCH$_2$CH$_2$CH$_2$CH$_2$CH$_2$—), 1.65 (m, —COCH$_2$CH$_2$CH$_2$CH$_2$CH$_2$—), 2.30 (t, —COCH$_2$CH$_2$CH$_2$CH$_2$CH$_2$—), 3.63 (s, —CCH$_2$), 4.03 (t, —COCH$_2$CH$_2$CH$_2$CH$_2$CH$_2$O—), 4.05 (s, —CH$_2$OCOCHCH$_2$—), 4.07 (s, —OCH$_2$CCH$_2$O—), 4.38 (m, —CCH$_2$); nuclear magnetic calculations m=11.4, x=6.3, y=43.9, n=51.2; GPC measured molecular weight: 14.6 kDa, molecular weight distribution: 1.38.

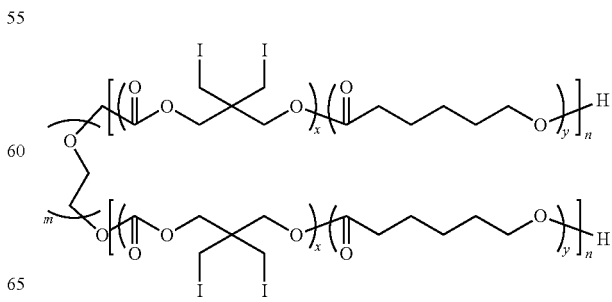

Example 10 Synthesis of Diblock Polymer Containing Double Iodine in the Side Chain NHS-PEG6.5k-PIC50k Under nitrogen atmosphere, 1 g (2.61 mmol) IC monomer was dissolved in 3 mL dichloromethane, added to a sealed reactor, and then 0.065 g (0.01 mmol) NHS-PEG6500 and 0.5 mL solution of zinc bis[bis(trimethylsilyl)amide] in dichloromethane (0.1 mol/L) were added. Then the reactor was tightly sealed, taken out of glove box. The reaction was allowed to proceed in oil bath at 40° C. for 2 days, and terminated by glacial acetic acid, precipitated in ice-cold ethyl ether. Finally, after filtration and vacuum drying, the NHS-PEG6.5k-PIC50k was obtained.

Example 11 Synthesis of Diblock Polymer Containing Double Iodine in the Side Chain Mal-PEG6k-PIC50k Under nitrogen atmosphere, 1 g (2.61 mmol) IC monomer was dissolved in 3 mL dichloromethane, added to a sealed reactor, and then 0.06 g (0.01 mmol) Mal-PEG6000 and 0.1 mol/L solution of zinc bis[bis(trimethylsilyl)amide] in dichloromethane (0.1 mL) were added. The reaction was allowed to proceed in oil bath at 40° C. for 2 days, post-treatment was the same as Example 2, the Mal-PEG6k-PIC50k was obtained.

Example 12 Synthesis of Targeting Diblock Polymer cNGQ-PEG6.5k-PIC50k

Two steps for the Synthesis of polymer cNGQ-PEG6.5k-PIC50k coupling ring type polypeptide cNGQGEQc (cNGQ), the first step was the same as Example 4 to prepare NHS-PEG6.5k-PIC50k; the amide reaction bonding of amido of cNGQ and the polymer as got above as the second step. Polymer said above NHS-PEG6.5k-PIC50k was dissolved in DMF, then two times the molar weight of cNGQ was added, the reaction was carried out at 30° C. for 2 days, then the free cNGQ which was not bonded was removed by dialysis, freeze-dried to give the final product cNGQ-PEG6.5k-PIC50k. The grafting ratio of cNGQ was 92%, by the analysis of nuclear magnetic and BCA protein kit.

A variety of biodegradable amphiphilic polymer containing double iodine in the side chain were obtained by the same way as above example, and the proportion of the raw materials and the characteristics are shown in table 1.

TABLE 1 preparation conditions of each polymer, nuclear magnetic resonance and GPC characterization results

| | Preparation dosage (mmol) | | | Number of repeating units (NMR) | | | Molecular weight and molecular weight distribution of products | |
|---|---|---|---|---|---|---|---|---|
| polymer | Initiator (PEG) | IC | Second monomer: CDC/TMC/LA/ TMBPEC or CL | m | x (IC) | y | Molecular weight (kg/mol) NMR | PDI |
| PEG5k-6-PIC100k | 0.01 | 2.61 | — | 114 | 262.8 | | 105.4 | 1.40 |
| PEG1.9k-6-PIC100k | 0.01 | 2.61 | — | 43 | 264.7 | | 103 | 1.37 |
| PEG6.5k-6-PIC100k | 0.02 | 5.23 | — | 148 | 264.1 | | 107.4 | 1.34 |
| PEG5k-6-PIC12.3k | 0.02 | 0.79 | — | 114 | 33 | | 17.6 | 1.36 |
| PEG5k-6-PIC7.6k | 0.02 | 0.52 | — | 114 | 21.5 | | 13.2 | 1.32 |
| PEG5k-b-PIC2.8k | 0.02 | 0.26 | — | 114 | 7.3 | | 7.8 | 1.34 |
| PEG1.9k-P(IC3.7k-co-CL3.8k) | 0.21 | 1 | 0.4 | 43 | 10 | 32 | 9.6 | 1.32 |
| PEG5k-PCL3.8k-PIC0.7k | 0.31 | 0.26 | 0.35 | 114 | 2 | 33 | 9.5 | 1.35 |
| PEG1.9k-PCL1.8k-PIC0.7k | 0.1 | 0.42 | 1.76 | 43 | 2 | 16 | 4.4 | 1.32 |
| PEG1.9k-6-PIC0.8k | 1 | 2.6 | — | 43 | 2.1 | | 2.7 | 1.30 |
| PEG5k-P(IC2.8k-co-TMBPEC3.2k) | 0.1 | 0.08 | 1.2 | 114 | 7.3 | 10 | 11.6 | 1.53 |
| PEG5k-P(IC4.9k-co-TMC19k) | 0.02 | 0.26 | 3.85 | 114 | 12.8 | 186 | 29.2 | 1.48 |
| PEG5k-PLA7.8k-PIC1.7k | 0.05 | 0.26 | 2.78 | 114 | 8.9 | 122 | 14.7 | 1.47 |
| PEG5k-P(CDC5k-co-IC50k) | 0.02 | 2.61 | 0.52 | 114 | 126.4 | 24 | 57.9 | 1.31 |
| PEG10k-6-PIC50K | 0.01 | 2.61 | | 227 | 125.7 | | 58 | 1.33 |
| NHS-PEG6.5k-P(CDC5k-co-IC50k) | 0.01 | 2.61 | 0.52 | 114 | 131.1 | 24 | 61.2 | 1.32 |
| Mal-PEG6k-P(CDC5k-co-IC50k) | 0.01 | 2.61 | 0.52 | 114 | 131.4 | 24 | 60.8 | 1.33 |

Figure 4:
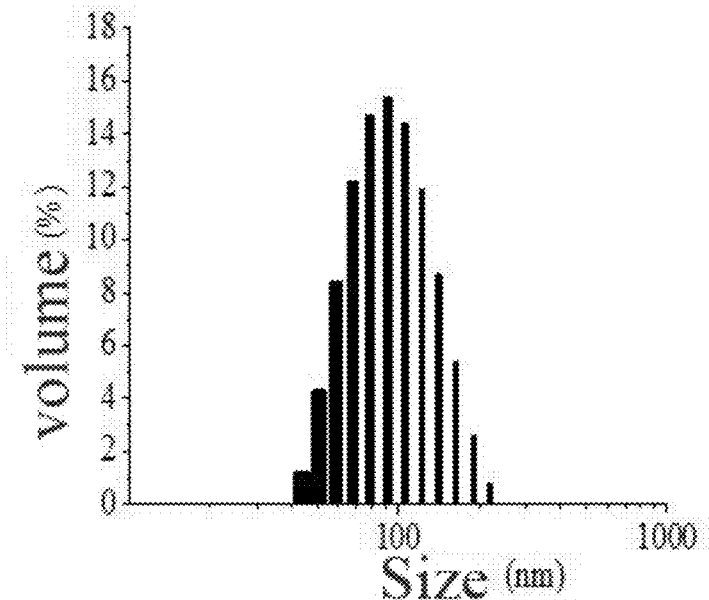
FIG. 4 is a graph showing the particle size distribution diagram of the nanoparticles of the biodegradable copolymer containing a group of double iodine in the side chain in Example 13.

Example 13 the Cytotoxicity of the Vesicle of PEG5k-P(CDC5.6k-Co-IC27.2k) was Tested with MTT Method The nano-vesicle of polymer PEG5k-P(CDC5.6k-co-IC27.2k) was prepared through dialysis. Specific process is: 5 mg of the polymer PEG5k-P(CDC5.6k-co-IC27.2k) was dissolved in 1 mL N,N-dimethylformide, then 4.0 mL of phosphate buffer solution (10 mM, pH 7.4, PB) was added dropwise under the stirring condition at 25° C. The solution obtained put into a beforehand dialysis bag (SPECTRA/POR, MWCO: 3500) after stirring for 1 hour; the cross-linked nano-vesicle were obtained by dialysis with phosphate buffer solution (10 mM, pH 7.4) for 24 h. The size of obtained nano-vesicle was 115 nm by dynamic light scattering particle size analyzer (DLS), and the particle size distribution was 0.11, which was showed in FIG. 4.

Figure 5:
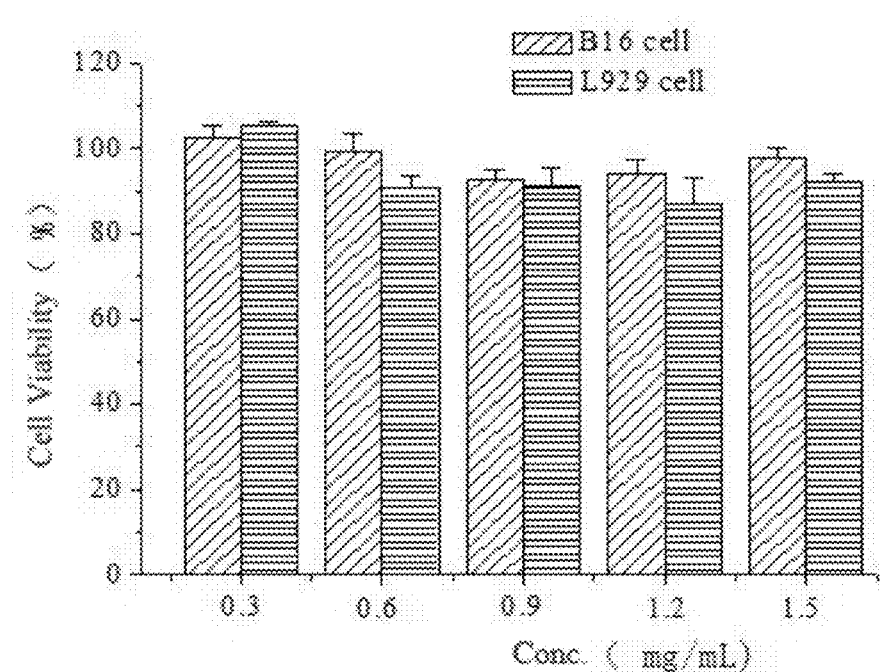
FIG. 5 is a graph showing the toxicity of the nanoparticles of the biodegradable copolymer containing a group of double iodine in the side chain on cells in Example 13.

The cytotoxicity of the nano-vesicle of PEG5k-P(CDC5.6k-co-IC27.2k) was tested with MTT method. The cells used were B16 (murine melanoma cells) and L929 (human fibroblasts). At 37° C. and 5% $CO_2$, the cell density was $1 \times 10^4$/bore in the Dulbecco s modified Eagle medium (DMEM) containing 10% serum. 24 hours later, the medium was replaced with 90 μL DMEM containing 10% serum and 10 μL different concentrations of PEG5k-P(CDC5.6k-co-IC27.2k) nano-vesicles (concentrations of 0.3, 0.6, 0.9, 1.2 and 1.5 mg/mL) and cells were cultured for 24 hours; then the medium was replaced with 100 μL fresh DMEM and 10 μL MTT solution (5 mg/mL) was added. Continue to culture for 4 hours and 100 μL generated crystals by DMSO dissolve was added. The optical density of the sample was measured at 570 nm with a BioTek micro disk measuring instrument. The result of cells were cultured alone in the DMEM medium of 10% serum as a standard and recorded as 100% survival. FIG. 5 is the survival rate of B16 cell (A) and L929 cells (B); can be seen from the figure, survival rate of B16 cell and L929 is still greater than 83% cell at the concentration of 1.2 mg/mL of nano-vesicles, indicating that the polymeric biocompatibility is very good.

Figure 6:
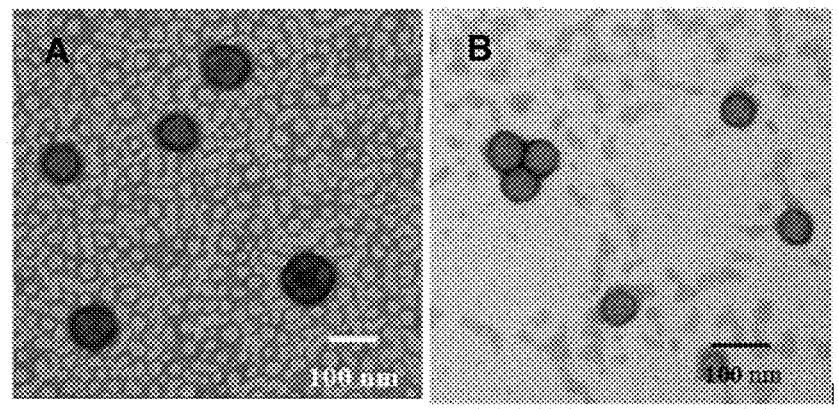
FIG. 6 is a graph showing the transmission electron microscopy (TEM) of the nanoparticles of the biodegradable polymer in Example 14.

Example 14 Synthesis of Nano-Vesicle of Biodegradable Polymer Containing Double Iodine in the Side Chain PEG-b-PIC The nano-vesicle of polymer PEG-b-PIC was prepared through dialysis. Specific process is: 5 mg of the polymer PEG-b-PIC (molecular weight of PIC is 12.3 kg/mol or 22.7 kg/mol) was dissolved in 1 mL N,N-dimethylformide, then 4.0 mL of phosphate buffer solution (10 mM, pH 7.4, PB) was added dropwise under the stirring condition at 25° C. The solution obtained put into a beforehand dialysis bag (SPECTRA/POR, MWCO: 3500) after stirring for 1 hour; the organic solvent was removed by dialysis with phosphate buffer solution (10 mM, pH 7.4) for 24 h. FIG. 6A, B respectively for transmission electron microscopy (TEM) of self-assembled nanoparticles of the ring biodegradable polymer PEG5k-b-PIC12.3k, PEG5k-b-PIC22.7k, it can be seen that the nanoparticles has a hollow vesicle structure.

Figure 7:
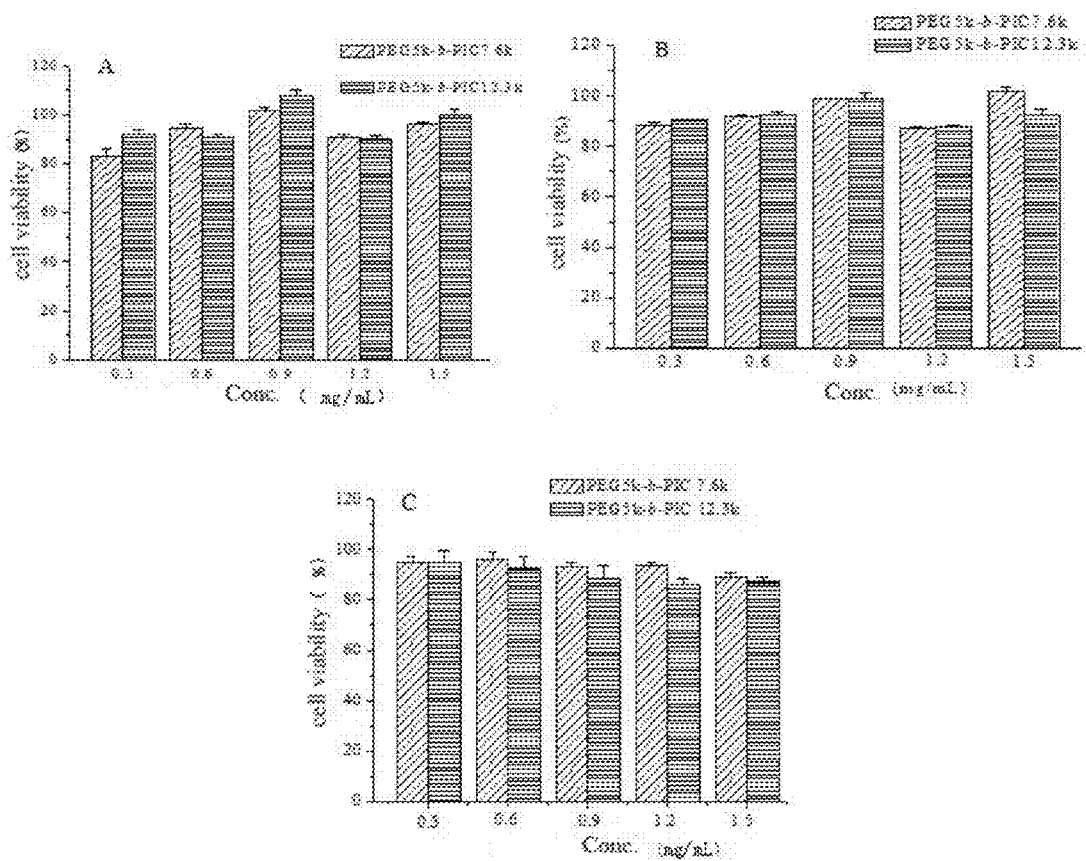
FIG. 7 is a graph showing the toxicity of the nanoparticles of the biodegradable polymer containing a group of double iodine in the side chain on cells in Example 15.

Example 15 the Cytotoxicity of the Micelle and Vesicle Prepared by Polymer Containing Double Iodine in the Side Chain PEG-b-PIC The cytotoxicity of the nano-vesicle of PEG5k-b-PIC12.3k and the nano-vesicle of PEG5k-b-PIC7.6k was tested with MTT method. The cells used were MCF-7 (human breast cancer cells), HepG2 (human hepatoma cells) and L929 (human fibroblasts). At 37° C. and 5% CO2, the cell density was 1×104/bore in the Dulbecco s modified Eagle medium (DMEM) containing 10% serum. 24 hours later, the medium was replaced with 90 μL DMEM containing 10% serum and 10 μL different concentrations of PEG-b-PIC nano-vesicles (concentrations of 0.3, 0.6, 0.9, 1.2 and 1.5 mg/mL) and cells were cultured for 24 hours; then the medium was replaced with 100 μL fresh DMEM and 10 μL MTT solution (5 mg/mL) was added. Continue to culture for 4 hours and 100 μL generated crystals by DMSO dissolve was added. The optical density of the sample was measured at 570 nm with a BioTek micro disk measuring instrument. The result of cells were cultured alone in the DMEM medium of 10% serum as a standard and recorded as 100% survival. FIG. 7 is the survival rate of MCF-7 cell (A), HepG2 cell (B) and L929 cell (C), can be seen from the figure, survival rate of cell is greater than 82% cell, indicating that the polymer PEG-b-PIC material has good biocompatibility.

Example 16 Loading of a Hydrophobic Anticancer Drug Doxorubicin by Micelle Nanoparticle of PEG5k-b-PIC7.6k Nano-vesicle loaded drug of biodegradable polymer containing double iodine in the side chain PEG5k-b-PIC7.6k was prepared through solvent exchange method. 4 mL phosphate buffer solution (10 mM, 7.4 pH) was added dropwise into the mixture of the solution of 1 mL DMF of PEG5k-b-PIC7.6k (5 mg/mL) and 100 μL the solution of doxorubicin in DMSO (DOX, 10% 5 mg/mL), put into dialysis sack (Spectra/Pore & MWCO, 3500) after 1 hour of ultrasound, and in the PB (10 mM, pH 7.4) in 12 hours of dialysis. The 100 μL solution of nanoparticle was freeze-dried and then dissolved in 3 mL DMF solution. The encapsulation efficiency was calculated by fluorescence spectrometer and combined with the standard curve of doxorubicin. From the results of measured fluorescence can be calculated, the drug loading efficiency was 82% and the drug loading was 8.07% when the theoretical drug loading of nano-sized micelles carrying hydrophobic doxorubicin was 10%. The above results indicated that the biodegradable polymer containing double iodine in the side chain PEG5k-b-PIC7.6k nanoparticles was wrapped with high efficiency to anticancer drug doxorubicin. In the same way, other hydrophobic drugs can be loaded into the polymer micelles.

The biodegradable polymer containing iodine obtained by the disclosure has small cytotoxicity and high encapsulation efficiency against cancer drugs, and can be used as a drug carrier with good compatibility.

Example 17 Synthesis of Diblock Polymer PEG5k-P(CDC5.6k-co-IC46.2k)

Under a nitrogen atmosphere, 0.026 g (0.14 mmol) CDC and 0.22 g (0.68 mmol) IC were dissolved in 1 mL dichloromethane, added to a sealed reactor, and then methoxy polyethylene glycol having 5000 molecular weight 0.022 g (0.0043 mmol) and 0.1 mol/L catalyst zinc bis[bis(trimethylsilyl)amide] in dichloromethane (0.1 mol/L) were added. Then the reactor was tightly sealed and taken out of glove box, put into oil bath at 40° C. The reaction was allowed to proceed for 2 days, and terminated by glacial acetic acid, precipitated in ice-cold ethyl ether. Finally, after filtration and vacuum drying, the diblock biodegradable polymer PEG5k-P(CDC5.6k-co-IC46.2k) was obtained. GPC measured molecular weight: 72.2 kDa, molecular weight distribution: 1.42.

Example 18 Preparation of the Cross-Linking Nano-Vesicle of Diblock Biodegradable Polymer PEG5k-P(CDC5.6k-Co-IC46.2k)

4.0 mL of phosphate buffer solution (10 mM, pH 7.4, PB) was added dropwise into the 1000 μL solution of DMF of polymer PEG5k-P(CDC5.6k-co-IC46.2k) (5 mg/mL). After placed for 2 hours, the organic solvent was removed by dialysis (MWCO: 3500) with PB for 24 h and the double-sulfur five-membered ring in the vesicle membrane can be self crosslinked by thiol disulfide exchange reaction, obtained crosslinked polymer vesicles, marked as CLPs. DLS test results show that the diameter of the crosslinked nanocapsules CLPs is 123 nm, and the particle size distribution is 0.13.

Example 19 Preparation of Targeting Polymer and the Targeting Nano-Vesicle (cRGD20/CLPs) Prepared from it with PEG5k-P(CDC5.6k-Co-IC46.2k) was Used to CT Imaging Under a nitrogen atmosphere, 0.026 g (0.14 mmol) CDC and 0.22 g (0.68 mmol) IC were dissolved in 1 mL dichloromethane, added to a sealed reactor, and then NETS-PEG has 6000 molecular weight 0.026 g (0.0043 mmol) and 0.1 mol/L catalyst zinc bis[bis(trimethylsilyl)amide] in dichloromethane (0.1 mol/L) were added. Then the reactor was tightly sealed and taken out of glove box, put into oil bath at 40° C. The reaction was allowed to proceed for 2 days, and terminated by glacial acetic acid, precipitated in ice-cold ethyl ether. Finally, after filtration and vacuum drying, the diblock biodegradable polymer NHS-PEG6k-P(CDC5.6k-co-IC46.2k) was obtained. The amidation reaction of the amino group of the polymer with a short peptide cRGD is carried out at 30° C., after the reaction of the polymer 0.2 g (0.00035 mmol) and cRGD 5.61 mg (0.0007 mmol) for 48 hours under a nitrogen atmosphere, then dialysis in the water, obtained final targeting polymer cRGD-PEG6k-P(CDC5.6k-co-IC46.2k).

Figure 8:
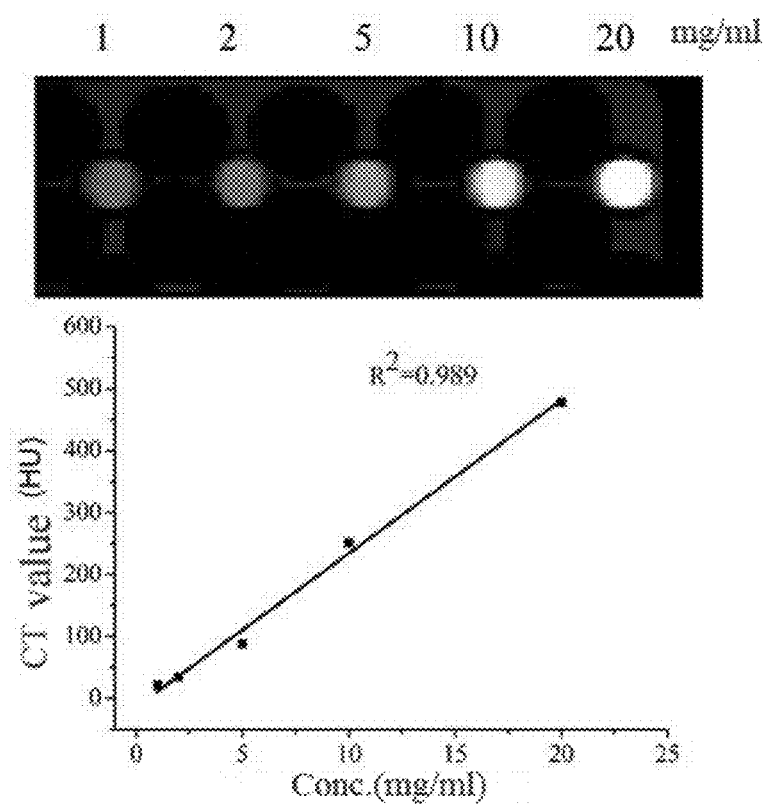
FIG. 8 is a graph showing the CT chart of the targeting nanoparticles of the biodegradable polymer containing a group of double iodine in the side chain in Example 19.

Mix 800 µL solution of DMF of polymer PEG5k-P(CDC5.6k-co-IC46.2k) (5 mg/mL) and 200 µL solution of DMF of polymer cRGD-PEG6k-P(CDC5.6k-co-IC46.2k) (5 mg/mL), 4 mL of phosphate buffer solution (10 mM, pH 7.4, PB) was added dropwise. After placed for 2 hours, the organic solvent was removed by dialysis (MWCO: 3500) with PB for 24 h and the double-sulfur five-membered ring in the vesicle membrane can be self crosslinked by thiol disulfide exchange reaction, obtained crosslinked targeting vesicle containing 20% cRGD, marked as cRGD20/CLPs. FIG. 8 is a graph showing the CT chart of the nano-vesicle, it can be seen that the CT value increases with the increase of vesicle concentration, and there is a good linear relationship between the vesicle concentration and the CT value. So, the polymer vesicles of the polymer containing iodine can be based on developing material.

Example 20 CT Imaging of Targeting Nano-Vesicle cRGD20/CLPs in and Out Mice

Figure 9:
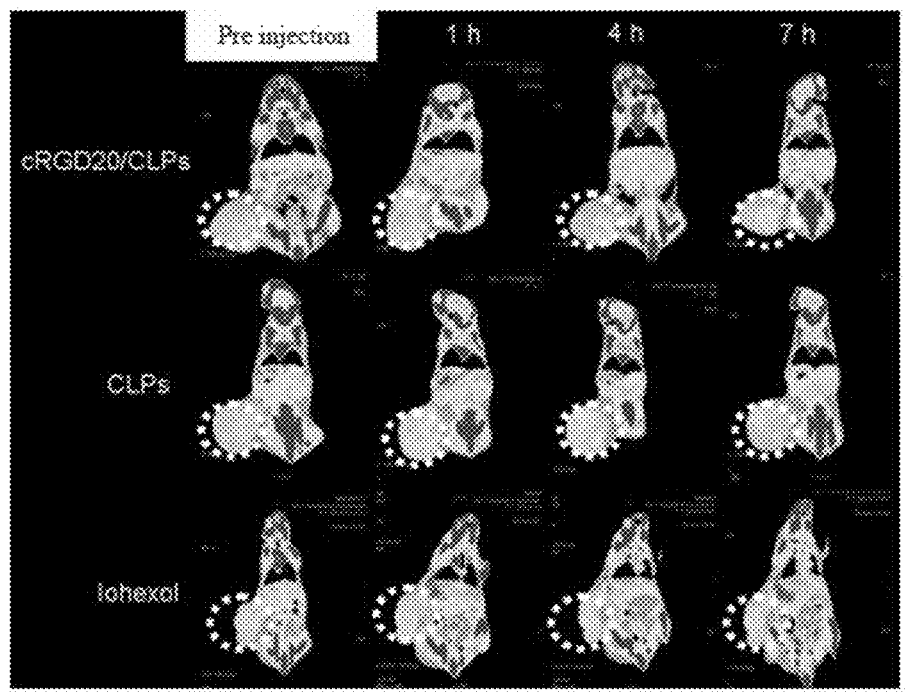
FIG. 9 is a graph showing the circulation of CT value of the nanoparticles of the biodegradable polymer containing a group of double iodine in the side chain were injected into the mice via tail veins in Example 20.
Figure 10:
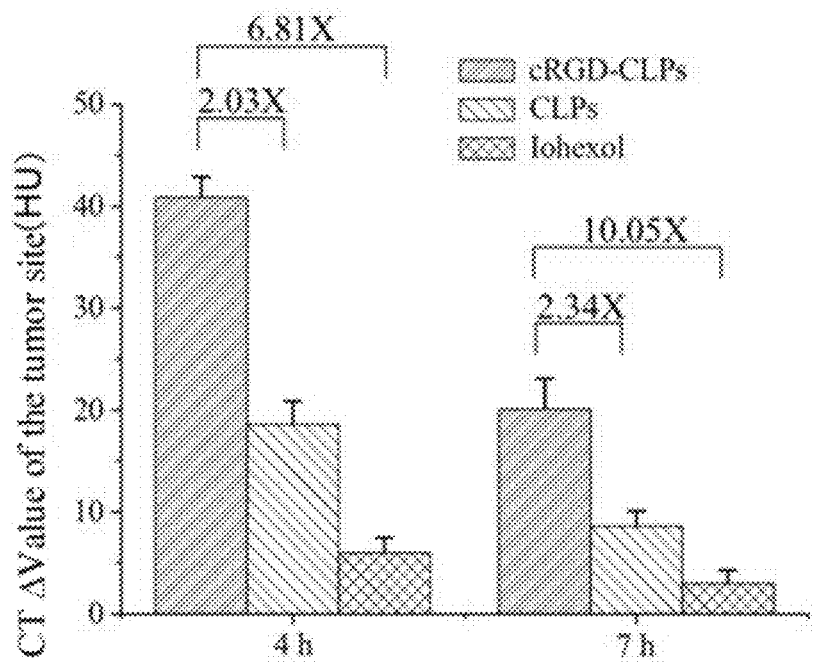
FIG. 10 is a graph showing the circulation of CT chart of the nanoparticles of the biodegradable polymer containing a group of double iodine in the side chain were injected into the mice via tail veins in Example 20.
Figure 11:
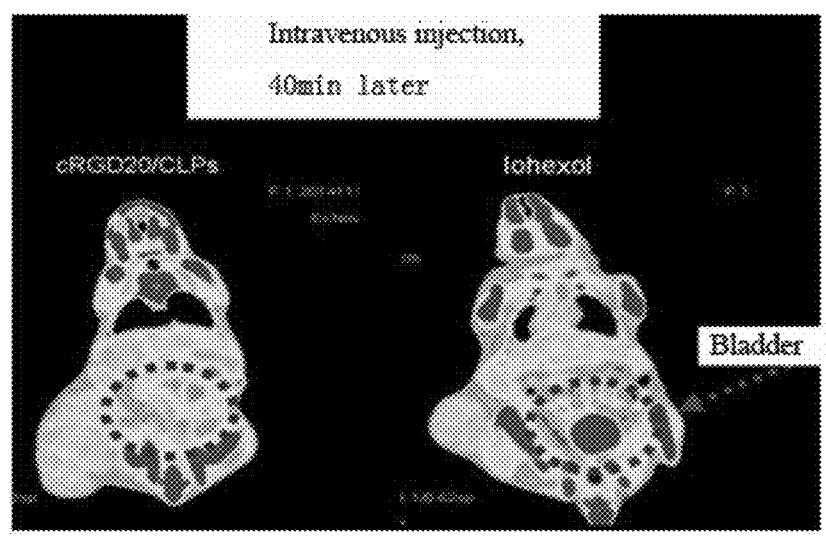
FIG. 11 is a graph showing the CT chart of the nanoparticles of the biodegradable polymer containing a group of double iodine in the side chain were injected into the bladder of mice via tail veins in Example 20.
Figure 12:
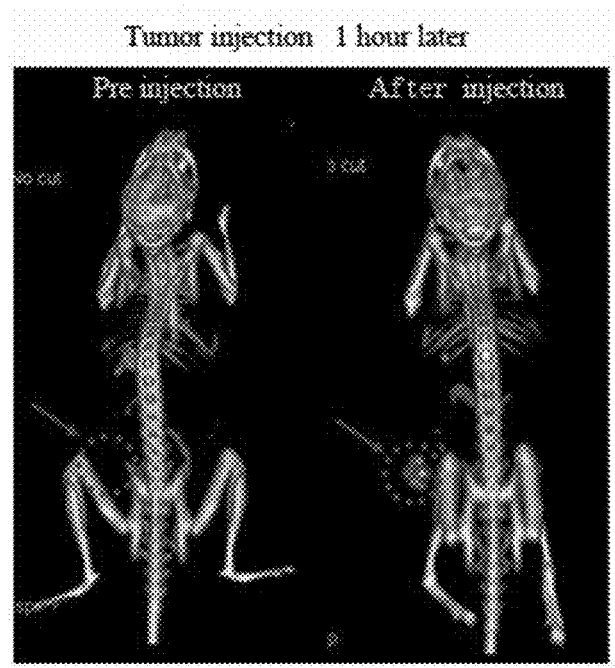
FIG. 12 is a graph showing the CT chart of the nanoparticles of the biodegradable polymer containing a group of double iodine in the side chain were injected into the mice via tail veins in Example 20.

Three groups of solutions were displayed to demonstrate the effect of CT in mice: the first group is targeted crosslinked nanocapsules cRGD20/CLPs (example 19), the second group consisted of non targeted nanocapsules CLPs (example 18), the third group was the control group, iodine alcohol (Iohexol) solution; the iodine content of the three groups was the same. After injection by the tail vein into the mouse, the CT contrast images were observed at different times. From FIG. 9 can be observed that after a 4 hour cycle of the cRGD20/CLPs in mice, CT image showed obvious enhancement effect, which indicates that cRGD20/CLPs can accumulate in the tumor site, CLPs accumulation at the tumor site is weaker, while the control group of iohexol did not develop the phenomenon. By the changing CT value in FIG. 10 can be seen, after a 4 hour cycle, CT change of cRGD20/CLPs was the highest, followed by CLPs, and lowest in the control group, after 7 hours of circulation, CT value of cRGD20/CLPs is 2 times and 10 times than the other two groups. From FIG. 11 can be seen in circulation after 40 minutes, iohexol group in the bladder has a contrast strong signal, while cRGD20/CLPs group is very weak, shown the cRGD20/CLPs relative to the small molecular contrast agent of iohexol is less vulnerable to clearance in circulation in mice, and there is a long cycle time. FIG. 12 shown the direct injection of cRGD20/CLPs at the tumor site in mice, and after 1 hours of circulation, there is a strong contrast signal before the injection.

Figure 13:
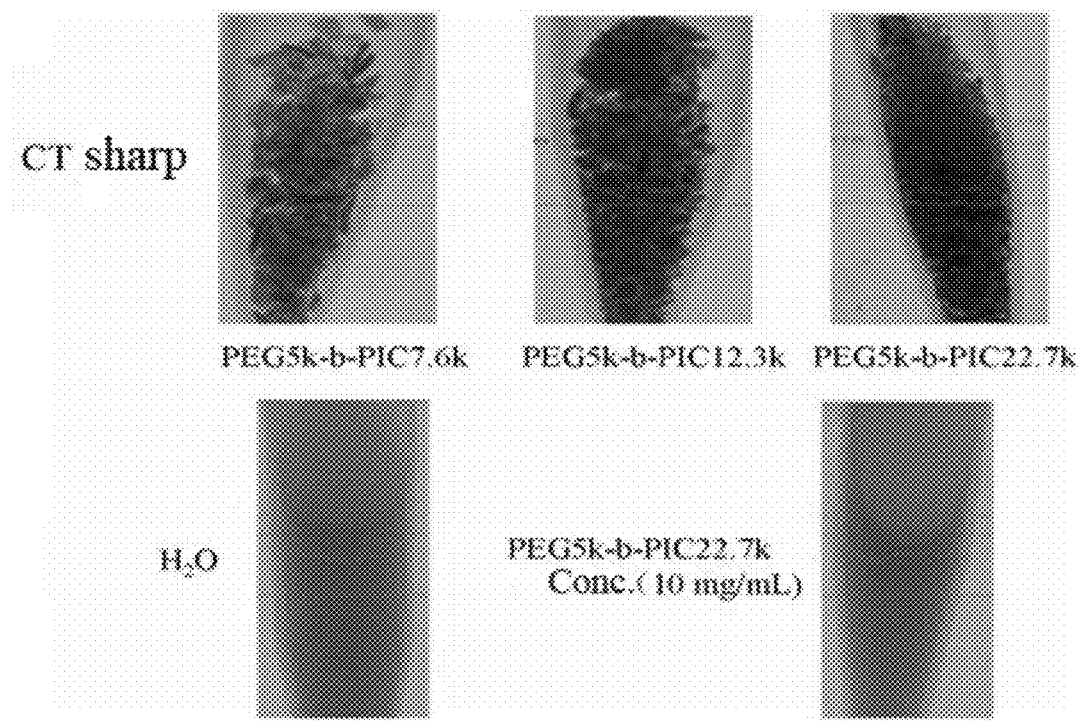
FIG. 13 is a graph showing the CT chart of the biodegradable polymer containing a group of double iodine in the side chain PEG-b-PIC in Example 21.

Example 21 CT Imaging of Nanoparticles of Biodegradable PEG-b-PIC Containing Double Iodine in the Side Chain FIG. 13 is a graph showing the CT chart of nanoparticles of the biodegradable polymer PEG-b-PIC (PEG5k-b-PIC7.6k micelle, PEG5k-b-PIC12.3k vesicle and PEG5k-b-PIC22.7k vesicle). It can be seen that with increase of PIC molecular in polymer, developing strength increased; at the same time, compared to water, nano-vesicle of PEG5k-b-PIC22.7k with developing the most obvious effect; therefore, the nano-vesicle and nano-sized micelle of biodegradable polymer containing double iodine in the side chain can be used as a developing material.

Figure 14:
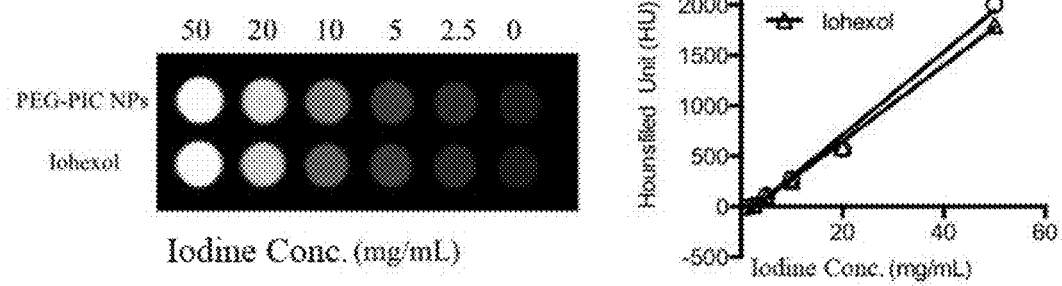
FIG. 14 is a graph showing the X-ray attenuation coefficient and the CT effect of the nanoparticles of the biodegradable polymer containing a group of double iodine in the side chain PEG-b-PIC in Example 22.

Example 22 Determination of In Vitro X Ray Attenuation Coefficient of Nano-Vesicle of PEG5k-b-PIC50k The solution of nano-vesicle with different iodine content of 50, 20, 10, 5, 2.5 mg/mL is obtained by enrichment of nano-vesicle PEG-b-PIC with different iodine content. FIG. 14 is a graph showing the X-ray attenuation coefficient and the CT effect of the PEG-b-PIC and iohexol. As shown in the figure, PEG-b-PIC nano-vesicles have the same in vitro X-ray attenuation coefficient as iohexol in the same amount of iodine, and the HU values are linearly related to the concentration. Thus, the nano-vesicles formed by PEG-b-PIC have very good X ray attenuation coefficients and can be used as a developer for CT imaging.

Figure 15:
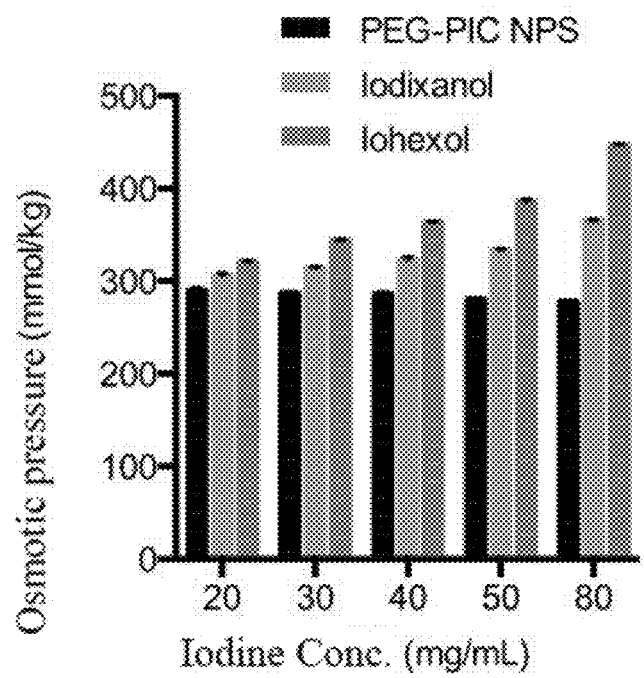
FIG. 15 is a graph showing the results of in vitro osmotic pressure of the nanoparticles of the biodegradable polymer containing a group of double iodine in the side chain PEG-b-PIC in Example 23.

Example 23 Determination of In Vitro Osmotic Pressure of Nano-Vesicle of PEG5k-b-PIC50k The solution of nano-vesicle with different iodine content of 80, 50, 40, 30, 20 mg/mL is obtained by enrichment of nano-vesicle PEG-b-PIC with different iodine content. FIG. 15 is a graph showing the results of in vitro osmotic pressure of the PEG-b-PIC, iohexol and iodixanol by dew point osmometer (WESCOR Vapro 5600) in PBS (7.4, 10 mM). As shown in Figure, osmotic pressure of nano-vesicle of PEG-b-PIC does not increase with increasing concentration, and is comparable to the osmotic pressure of the blood. Compared with a conventional small molecule contrast agent, the nano-vesicle of PEG-b-PIC in the present invention do not produce side effects of osmotic pressure.

Figure 16:
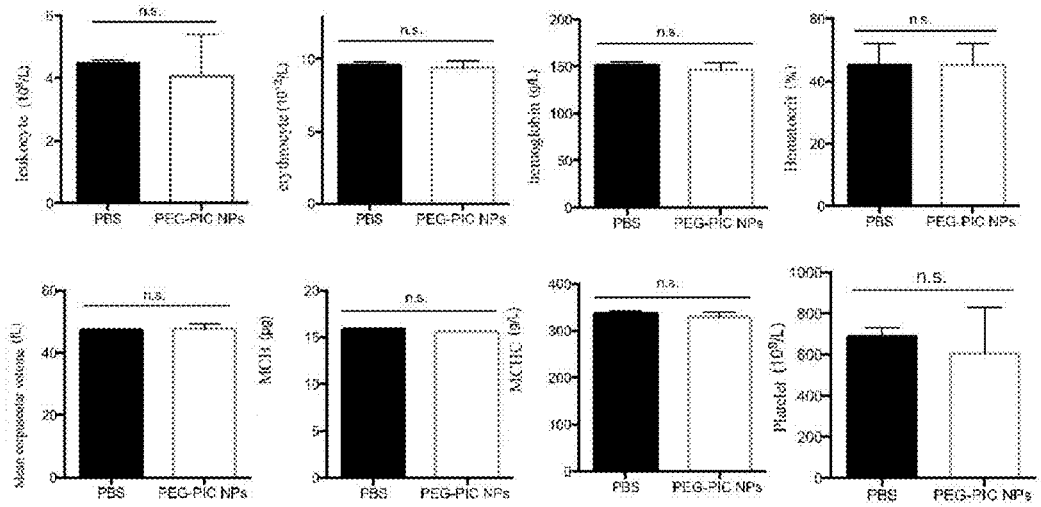
FIG. 16 is a graph showing the blood routine test in the in vivo acute toxicity test of the nanoparticles of the biodegradable polymer containing a group of double iodine in the side chain PEG-b-PIC in Example 24.
Figure 17:
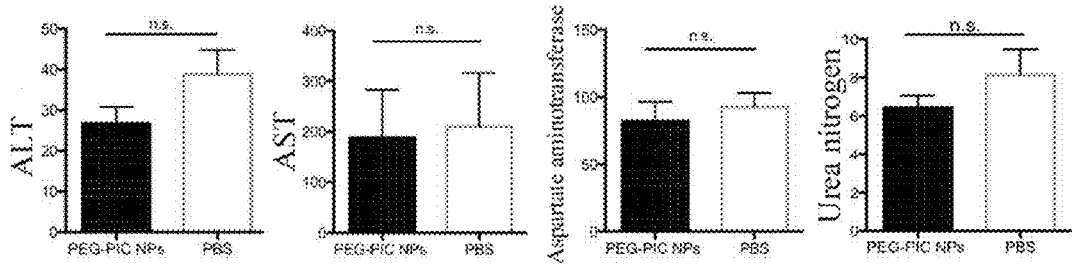
FIG. 17 is a graph showing the blood biochemical tests in the in-vivo acute toxicity laboratory of the nanoparticles of the biodegradable polymer containing a group of double iodine in the side chain PEG-b-PIC in Example 24.

Example 24 Determination of Acute Toxicity In Vivo for Nano-Vesicle of PEG5k-b-PIC50k 50 mgI/mL polymer nano-vesicle were injected into the mouse by tail vein (200 µL) and sacrificed after 24 hours for blood collection. The blood routine and blood biochemical data were measured in FIG. 16 and FIG. 17, the data showed the contrast medium showed no acute toxicity in vivo at the dose of 500 mgI/mL and had no effect on liver and kidney function.

Figure 18:
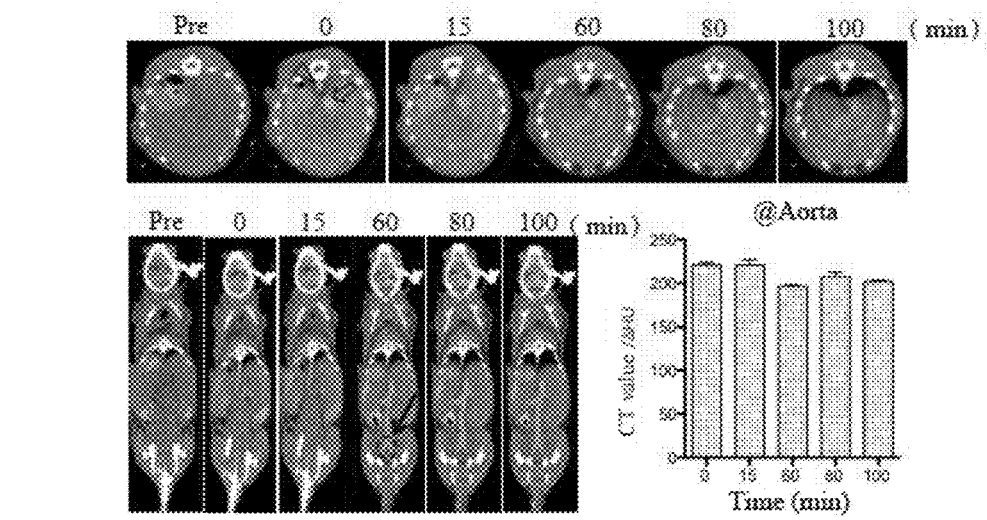
FIG. 18 is a graph showing the CT images of hematology of the nanoparticles of the biodegradable polymer containing a group of double iodine in the side chain PEG-b-PIC in Example 25.

Example 25 In Vivo Imaging of Nano-Vesicle of PEG5k-b-PIC50k as Blood Pool Contrast Agent 50 mgI/mL polymer nano-vesicle were injected into the mouse C57/BL6 by tail vein (200 µL) and CT images of different time intervals were collected, as 0 hour, 15 minutes, 60 minutes, 80 minutes, and 100 minutes, respectively, to observe the effect of PEG-b-PIC nanoparticles as a blood pool. As shown in FIG. 18, the aortic and inferior vena cava can be seen markedly enhanced in 0 hours from the coronal plane, and visible and clear vascular images can be seen from the CT image at 60 minutes from the missing surface. After calculation, the CT value increased by 220 and lasted for 100 minutes, the CT value was enhanced by more than

Figure 19:
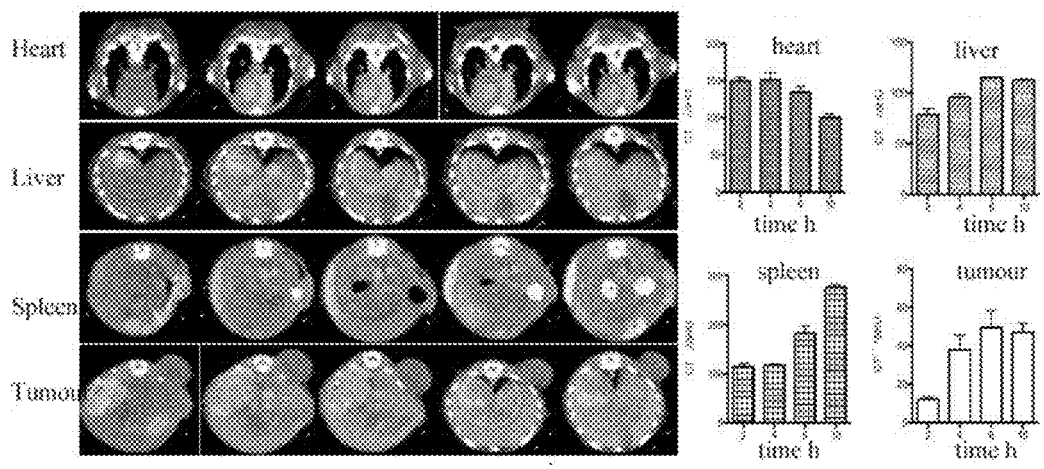
FIG. 19 is a graph showing the CT images of cRGD-PEG-b-PIC nanoparticles containing a group of double iodine in the side chain and neovascular targeting molecule cRGD on U87MG gliomas in Example 26.
Figure 20:
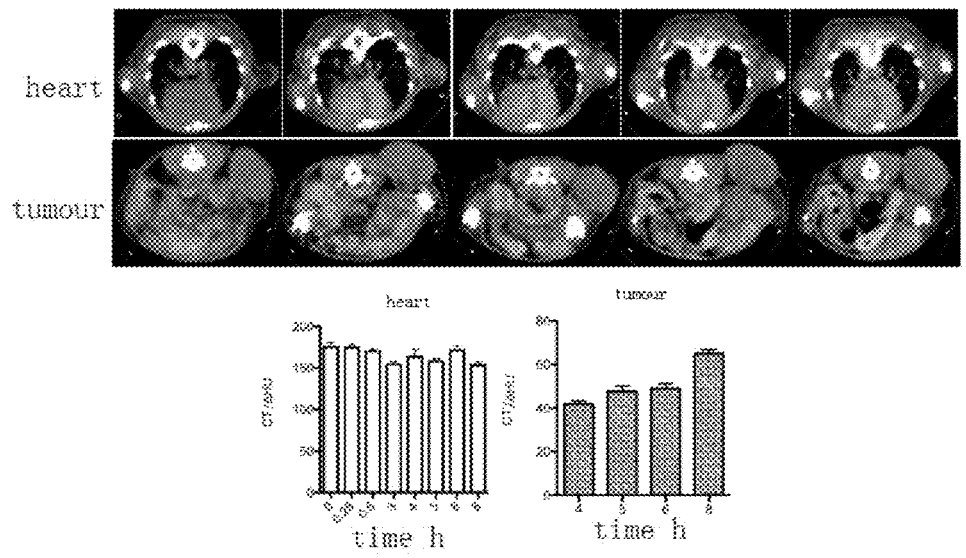
FIG. 20 is a graph showing the CT images of cRGd-PEG-b-PIC nanoparticles containing a group of double iodine in the side chain and neovascular targeting molecule cRGD on MCF-7 human breast cancer in Example 26.

Example 26 Nano-Vesicle of cRGD Targeted cRGD-PEG5k-b-PIC50k as Targeted Nano-Sized Contrast Agents for Tumor Neovascularization 50 mgI/mL polymer nano-vesicle with cRGD-PEG-b-PIC were injected into the tumour-bearing nude mice by tail vein (200 µL) and subcutaneous model of U87MG glioma and human breast cancer MCF-7 were selected as new vascular targeting model for CT imaging, and the CT images at different time points were collected to demonstrate the targeting ability of the tumor neovascularization. As noted in FIG. 19, the CT values of the U87MG tumor bearing mice is increased 150HU at two hours and still increased 100HU at 10 hours at the heart site. CT enhancement reached 75HU at two hours, and gradually increased with time, reaching 100HU at 10 hours at the liver. The enhancement at the spleen site reached 270HU at 10 hours. At the tumor site, the CT value increased to 50HU at 6 hours. These results indicate that the nano-vesicle can target the neovascularization of U87MG glioma. From FIG. 20, we can see that the CT value of MCF-7 tumor bearing mice is 150HU after increased for 8 hours, and CT in tumor sites increased to 65HU. These results indicate that the nano-vesicle can target the new blood vessels of MCF-7 human breast cancer very well.

Figure 21:
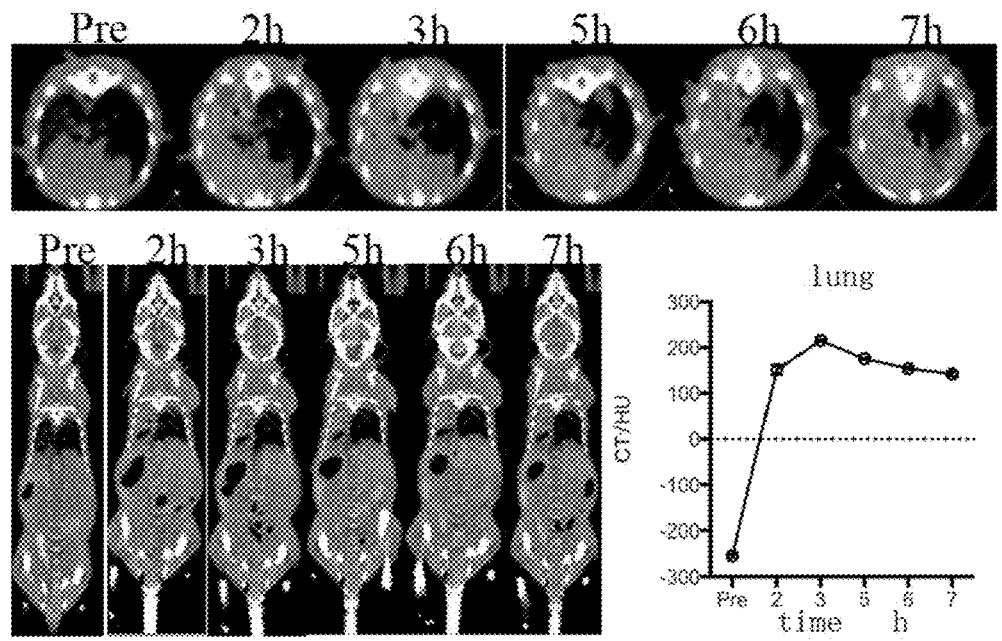
FIG. 21 is a graph showing the CT images of cRGd-PEG-b-PIC nanoparticles containing a group of double iodine in the side chain and neovascular targeting molecule cRGD on A549 in situ lung cancer in Example 27.
Figure 22:
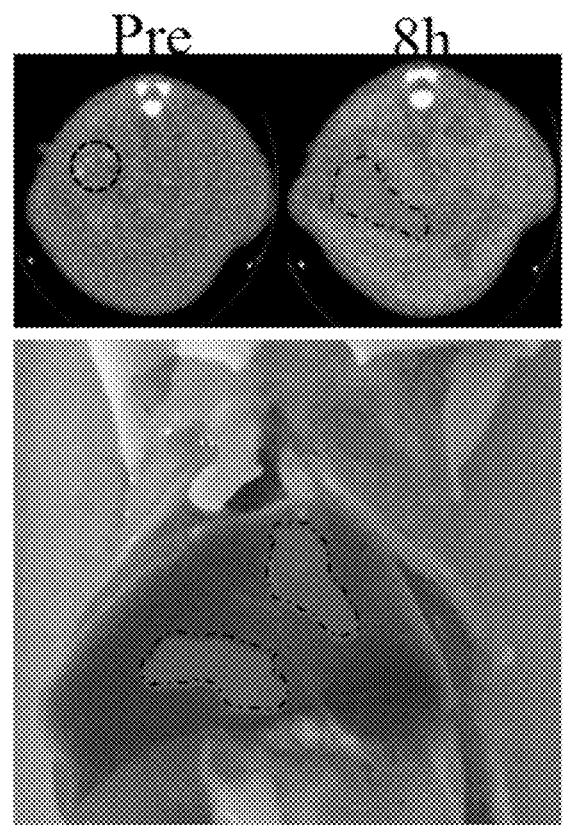
FIG. 22 is a graph showing the CT images of PEG-b-PIC nanoparticles containing a group of double iodine in the side chain on SMMC-7721 in situ hepatocellular carcinoma in Example 28.

Example 27 cRGDNGQ Targeted cNGQRGD-PEG5k-b-PIC50k Nano-Vesicle as a Targeted Contrast Agent for Neovascularization in Lung Cancer In Situ 50 mgI/mL nano-vesicle with cNGQRGD-PEG-b-PIC was injected through tail vein (200 L) into tumor bearing A549 non-small cell lung cancer in situ tumor model in nude mice. CT images collected at different time points were collected to demonstrate the targeting ability of the in situ tumor. By FIG. 21, the CT values of the A549 tumor bearing mice increased to 400HU at 2 hours, and increased by more than 400HU at 7 hours. It can be explained that cNGQ modified vesicles can be used as contrast agents for targeting A549 in situ lung cancer.

Example 28 Nano-Vesicle of PEG5k-b-PIC50k as a Contrast Agent In Situ Liver Cancer 50 mgI/mL nano-vesicle of PEG-b-PIC was injected through tail vein (200 L) into nude mice bearing SMMC-7721 in situ hepatoma. CT images at different time points were collected to demonstrate that the vesicles were used as an in situ liver cancer contrast agent. The darker part of the liver is the site of the tumor at 8 hours. Compared to normal liver cells, cancer cells consume fewer unembellished vesicles, so the tumor site is darker than the surrounding normal cells in CT imaging. Thus it can be concluded that PEG-b-PIC nano-vesicle can be used as nano contrast agents for SMMC-7721 in situ liver cancer and are useful for the diagnosis of hcc.

Example 29 Hydrophilic Drug Doxorubicin Hydrochloride Carrying, In Vitro Release of the Targeted Crosslinked Nano-Vesicle of cRGD20/CLPs Polymer vesicle was prepared through solvent exchange method and the loading of DOX.HCl was carried out by pH gradient method and the hydrophilic drug DOX.HCl was encapsulated by the difference of pH inside and outside of vesicles. The mixture of 800 µL solution of DMF of polymer PEG5k-P(CDC5.6k-co-IC46.2k) (5 mg/mL) and 200 µL solution of DMF of polymer cRGD-PEG6k-P(CDC5.6k-co-IC46.2k) (5 mg/mL) was added dropwise into 4000 µL citric acid/sodium citrate buffer solution (10 mM, 4 pH), and placed in shaking table (200 rmp) for 5 hours at 37° C. to form the vesicles, then 0.05 mL of PB (4 M, pH 8.1) was added to establishing pH gradients, and PB solution with DOX.HCl was immediately joined, allowing the drug into the vesicles by placing shaking table for 5-10 hours. Finally, was loaded into the dialysis bag (MWCO 7000) and dialysis in PB (10 mM, pH 7.4) for 24 hours, then the organic solvent and the free drug were taken out, the vesicles were automatically crosslinked, and the water was changed five times to get the cRGD20-CLPs loading DOX.HCl. The vesicles with different ratios of drugs (10%-30%) had a particle size of 105-124 nm and a particle size distribution of 0.10-0.15. The encapsulation efficiency of DOX.HCl was 63%-77% by fluorescence spectrometer. This method can be efficiently loaded hydrophilic anticancer drugs epirubicin hydrochloride, irinotecan hydrochloride and Mitoxantrone Hydrochloride, efficiency in 50-80%.

The experiment of DOX.HCl in vitro release was performed in a thermostatic shaker at 37° C. under 200 rpm shaking. Each group had three samples. Group 1: DOX.HCl-loaded self-crosslinked vesicle were released in PB (10 mM, pH 7.4) which simulated the intracellular reducing environment through the addition of 10 mM glutathione (GSH); Group 2: the release of crosslinked. DOX.HCl-loaded polymer nanoparticles in PB (10 mM, pH 7.4); the concentration of the drug-loaded self-crosslinked vesicle was 30 mg/L; 0.6 mL of the solution was taken and put into a dialysis bag (MWCO: 12,000) for release, the corresponding solvents for dialysis (25 mL) were added to each tube. At the predetermined time interval, 5.0 mL of the medium exterior the dialysis bag was taken out for the test, meanwhile 5.0 mL of the corresponding medium was supplemented into the tubes. The drug concentration in the solution was determined with fluorescence spectrophotometer. The relationship between the cumulative release amount of doxoruhicin and time can be shown that, after adding the reducing substance glutathione (GSH) which simulates the cancer cells, the release was significantly faster than the condition that GSH component was not added. It suggests that in the presence of 10 mM reducing substance GSH, the drug-loaded self-crosslinked vesicles are able to effectively release the drug.

Example 30 Determination of Blood Circulation of Drug-Loaded CLPs Crosslinked Vesicle and Targeted Crosslinked Vesicle of cRGD20/CLPs DOX.HCl-loaded cRGD20/CLPs (Example 29), DOX.HCl-loaded CLPs, non crosslinked vesicle PEG5k-PIC46.2k and free DOX.HCl was injected through tail vein into nude Balb/C mice (with DOX of 10 mg/kg). The blood samples (approximately 10 µL) were collected at time points of 0, 0.25, 0.5, 1, 2, 4, 8, 12 and 24 h. The exact weight of the blood was determined through weighing by difference method, then 100 µL Triton (concentration: 1%) and 500 µL DMF (which contained 20 mM DTT, 1 M HCl) were added. The sample was subjected to extraction, followed by centrifugation (20,000 rpm, 20 min). Then the supernatant was collected, the amount of DOX.HCl at each time point was determined through fluorescence. The results show that the targeted drug loaded crosslinked vesicle, drug loaded crosslinked vesicles and drug loaded vesicles without crosslinking in vivo elimination half-life were 6.84, 6.46 and 3.73 hours, while DOX.HCl is only 0.13 hours, so the targeted drug loaded self crosslinking vesicles stable in the mice and has a long cycle time. The blood circulation tests of other drug targeted self-crosslinking vesicles and drug carrying self-crosslinking vesicles are similar in operation and calculation.

Example 31 Living Imaging of CLPs Crosslinked Vesicle and Targeted Crosslinked Vesicle of cRGD20/CLPs of B16 Bearing Melanoma Mice Nude Balb/C mice with body weight of about 18-20 g, aged 4-6 weeks were used in the experiment, $5 \times 10^6$ B16 melanoma cells were subcutaneously injected. After 3-4 weeks, when the size of the tumors was 100-200 mm$^3$, the experiment began. DOX.HCl-loaded cRGD20/CLPs (Example 29), DOX.HCl-loaded CLPs, and free DOX.HCl as the example. cRGD20/CLPs and CLPs which was labeled with the fluorescent material cy-7 was injected through tail vein into mice, then a small animal in vivo imaging was used to track the whereabouts of vesicles at different time points of 1, 2, 4, 6, 8, 12, 24, 48 hours. The results showed that cRGD20-CLPs accumulated rapidly in the tumor site, and the fluorescence remained strong after 48 hours. These results indicate that cRGD20-CLPs can target and enrich the tumor site. The in vivo imaging experiments of other targeted crosslinked vesicles and cross-linked vesicles are similar in operation and calculation.

Example 32 the Biological Distribution of Drug-Loaded CLPs Crosslinked Vesicle and Targeted Crosslinked Vesicle of cRGD20/CLPs to the SKOV3 Ovarian Cancer-Bearing Mice The tumor inoculated and administered intravenously is the same as Example 31. DOX.HCl-loaded cRGD20/CLPs (Example 29), DOX.HCl-loaded CLPs and free DOX.HCl was injected through tail vein into mice (DOX.HCl: 10 mg/kg). After 12 hours, the mice were euthanized. The tumor, and the heart, liver spleen, lung and kidney tissue were taken out, washed and weighed. Then 500 µL of 1% Triton was added, the samples were minced with a homogenizer, extracted after adding 900 µL DMF (which contained 20 mM DTT, 1M HCl). After centrifugation (20,000 rpm, 20 min), the supernatant was collected, the amount of DOX.HCl at each time point was determined through fluorescence. The results showed that The accumulation amounts of DOX.HCl of cRGD20/CLPs, CLPs and DOX-.HCl in tumor at 12 h are 6.68, 2.81, 0.61 ID %/g respectively (the amount of DOX per gram tumor or tissue against the total amount of injected DOX), cRGD20/CLPs which are 2.4 or 11 times larger than those of CLPs and DOX.HCl. It indicates that through EPR effect, the drug-loaded cRGD20/CLPs accumulate more at the tumor sites.

Example 33 Drug-Loaded Targeting Crosslinked Vesicles cRGD20/CLPs and Crosslinking Vesicles to Air the Maximum Tolerated Dose of Balb/C Mice (MTD)

Nude Balb/C mice with body weight of about 18-20 g, aged 4-6 weeks were used. Drug-loaded cRGD20/CLPs (doxorubicin concentration of 60 and 80 mg/kg), empty cRGD20/CLPs (polymer 300 and 400 mg/kg) and free adriamycin (5 and 10 mg/kg) was single injected, with five mice in each group, the last 10 days, the daily state of mind and body weight measurement was observed. The standard for MTD was non accidental death in mice or weight less than 15% in mice. Results showed that the MTD of drug targeting crosslinking vesicles is greater than 80 mg/kg, the MTD of empty cRGD20-CLPs is greater than 400 mg/kg, while the MTD of DOX is less than 10 mg/kg, the drug targeting crosslinking vesicles have high resistance to the mice, greatly improve the therapeutic window.

Example 34 Antitumor Effect and Weight Change in Mice Bearing B16 Tumor of Drug-Loaded Targeting Crosslinked Vesicles cRGD20/CLPs and Crosslinking Vesicles CLPs Nude Balb/C mice with body weight of about 18-20 g, aged 4-6 weeks were used in the experiment, $5 \times 10^6$ B16 cells were subcutaneously injected. After 2 weeks, when the size of the tumors was 30-50 mm$^3$, the experiment began. DOX.HCl-loaded cRGD20/CLPs (Example 29), no targeting DOX.HCl-loaded crosslinking vesicles CLPs, and free DOX.HCl and PBS was injected through tail vein into mice (DOX.HCl: 10 mg/kg) at 0, 4, 8, 12 day respectively. From Day 0 to 18, the body weight of the mice in each group was weighed every two days. The size of the tumor was precisely measured with Vernier scale, where the method for calculating the volume of tumors was: $V=(L \times W \times H)/2$, (where L was the length of the tumor, W was the width of the tumor, H was the thickness of the tumor). The survival of the mice was observed continuously till the 45th day. After 19-day treatment with cRGD20/CLPs, the tumors were obviously inhibited, there is a certain increase in the tumor of CLPs. However, though DOX.HCl may also inhibit tumor expansion, meanwhile the body weight of the mice in DOX.HCl group decreased 20% in 7 days, it had severe toxic side effect on the mice. By comparison the body weight of the mice of cRGD20/CLPs and CLPs was almost not changed, indicating that the drug-loaded crosslinked vesicle had no toxic side effects on the mice. Therefore, the drug-loaded targeting crosslinked vesicles can effectively inhibit tumor growth, and have no toxic side effect on the mice.

Example 35 CT Imaging of Drug-Loaded Targeting Crosslinked Vesicles cRGD20/CLPs in Mice Bearing B16 Tumor 50 mgI/m of the samples as Example 34 was injected through tail vein into mice bearing B16 tumor, as Example 26. The CT images at different time points were collected to demonstrate the targeting ability of the tumor. The results showed that at the tumor site of B16 tumor bearing mice, the CT value increased 140HU at 6 hour; at the heart site, the CT value increased 200HU at 2 hour and still increased 120HU at 12 hour; at the liver site, the CT value increased 85HU at 2 hour and gradually increased with time, reached 100HU at 10 hour; at the spleen site, the CT value increased 270HU at 10 hour. It indicates that the vesicles can be used either for therapy or for tumor imaging. The drug targeting nano-vesicle can also be used for the diagnosis and treatment of in situ lung cancer.

These results showed that targeted nano-vesicle of polymer containing iodine in the disclosure can in vivo imaging, for the preparation of the developer, has a wide application prospect in the diagnosis of tumor and other diseases.

What is claimed is:
1. A biodegradable polymer containing a functional group of double iodine in the side chain, which includes cyclic carbonate monomer containing double iodine, wherein the biodegradable polymer containing a functional group of double iodine is polymerized of cyclic carbonate monomer containing double iodine by one of the following steps:

(1) homopolymerize by cyclic carbonate monomer containing double iodine; or (2) cyclic carbonate monomer containing double iodine has copolymerization with cyclic carbonate containing double sulfur or trimethylene cyclic carbonate;

said cyclic carbonate monomer containing double iodine is

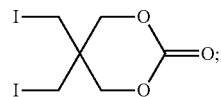

the molecular weight of said biodegradable polymer containing a functional group of double iodine in the side chain is 3-500 kDa;

said biodegradable polymer containing a functional group of double iodine in the side chain has a polydispersity index (PDI) of 1.30 to 1.53; and said biodegradable polymer containing a functional group of double iodine in the side chain forms nano-vesicles after dialysis.

2. The biodegradable polymer containing a functional group of double iodine in the side chain according to claim 1, wherein the amount of iodine in the molecular chain of aforesaid biodegradable polymer containing a functional group of double iodine in the side chain is 5%-65%.

3. The biodegradable polymer containing a functional group of double iodine in the side chain according to claim 1, wherein the cyclic carbonate monomer containing double iodine is polymerized in the presence of polyethylene glycol, ethylene glycol, isopropanol or propynol as the initiator and zinc bis [bis(trimethylsilyl) amide] as the catalyst.

4. The biodegradable polymer containing a functional group of double iodine in the side chain according to claim 1, wherein when the cyclic carbonate monomer containing double iodine is polymerized, the polymerization temperature is 40° C. and the polymerization time is 24-72 hours.

* * * * *